US007662568B2

(12) United States Patent
O'Leary et al.

(10) Patent No.: US 7,662,568 B2
(45) Date of Patent: Feb. 16, 2010

(54) IMMUNOLIPOSOME-NUCLEIC ACID AMPLIFICATION (ILNAA) ASSAY

(75) Inventors: Timothy J. O'Leary, Silver Spring, MD (US); Jeffrey T. Mason, Gaithersburg, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 12/399,060

(22) Filed: Mar. 6, 2009

(65) Prior Publication Data
US 2009/0176250 A1 Jul. 9, 2009

Related U.S. Application Data

(62) Division of application No. 10/759,099, filed on Jan. 20, 2004, now Pat. No. 7,582,430.

(51) Int. Cl.
C12Q 1/68 (2006.01)
(52) U.S. Cl. .................. 435/6; 435/91.1; 435/91.2; 536/23.1; 536/24.33
(58) Field of Classification Search ........... None
See application file for complete search history.

(56) References Cited

U.S. PATENT DOCUMENTS

| | | | |
|---|---|---|---|
| 4,704,355 | A | 11/1987 | Bernstein |
| 4,708,933 | A | 11/1987 | Huang et al. |
| 4,957,735 | A | 9/1990 | Huang |
| 5,227,170 | A | 7/1993 | Sullivan |
| 5,389,523 | A | 2/1995 | Plant et al. |
| 5,494,803 | A | 2/1996 | Carbonell et al. |
| 5,604,099 | A | 2/1997 | Erlich et al. |
| 5,656,493 | A | 8/1997 | Mullis et al. |
| 5,665,539 | A | 9/1997 | Sano et al. |
| 5,716,784 | A | 2/1998 | Di Cesare |
| 5,776,487 | A | 7/1998 | Maxfield Wilson et al. |
| 5,858,665 | A | 1/1999 | Hepp et al. |
| 5,922,553 | A | 7/1999 | Eberwine et al. |
| 6,013,442 | A | 1/2000 | Kolesar et al. |
| 6,261,771 | B1 | 7/2001 | Bohannon |
| 6,268,148 | B1 | 7/2001 | Barany et al. |
| 6,326,147 | B1 | 12/2001 | Oldham et al. |
| 6,461,817 | B1 | 10/2002 | Alland et al. |
| 6,503,452 | B1 | 1/2003 | Boxer et al. |
| 2003/0104506 | A1 | 6/2003 | Durst et al. |
| 2004/0258570 | A1 | 12/2004 | Beebe et al. |
| 2005/0079520 | A1 | 4/2005 | Wu |

FOREIGN PATENT DOCUMENTS

WO    WO9922772 A    5/1999

OTHER PUBLICATIONS

Pagnan et al. Journal of the National Cancer Institute, vol. 92:253-261. 2000.*

Brignole, C., et al., "Targeted Delivery System for Antisense Oligonucleotides: A Novel Experimental Strategy for Neuroblastoma Treatment," Cancer Letters, New York, NY US, vol. 197, No. 1/2, Jul. 18, 2003, pp. 231-235.

Kawaura, C, et al., "Monosialoganglioside containing cationic liposomes with a cationic cholesterol derivative promote the efficiency of gene transfection in mammalian culture cells," Biological and Pharmaceutical Bulletin, vol. 23, No. 6, Jun. 2000, pp. 778-780.

Mason, J, et al., "Liposome polymerase chain reaction assay for the sub-attomolar detection of cholera toxin and botulinum neurotoxin type A.," Nature Protocols 2006, vol. 1, No. 4, 2006, pp. 2003-2011.

Pagnan, G., et al, "Delivery of C-MYB Antisense Oligodeoxynucleotides to Human Neuroblastoma Cells Via Disialoganglioside GD2-Targeted Immunoliposomes: Antitumor Effects," Journal of the National Cancer Institute, US Dept. of Health, Education and Welfare, Public Health, US, vol. 92, No. 3, Feb. 2, 2000, pp. 253-261.

Alfonta, Lital et al., "Liposomes Labeled with Biotin and Horseradish Peroxidase: A Probe for the Enchanced Applification of Antigen-Antibody or Oligonucleotide-DNA Sensing Processes by the Preceipitation of an Insoluble Product on Electrodes", Analytical Chemistry, Jan. 1, 2001, vol. 73, No. 1, pp. 91-102.

Bailey, Austin L. et al., "Efficient Enacapsulation of DNA Plasmids in Small Neutral Liposomes Induced by Ethanol and Calcium", Biochmica et Biophysica Acta, 2000, vol. 1468, pp. 239-252.

Bridges, Michael Al. et al., "Fluorometric Determination of Nanogram Quantities of Protein in Small Samples: Application to Calcium-transport Adenosine Triphosphatase", Cli. Chim Acta 157, pp. 73-79.

Chaurand Pierre, et al., "Direct Profiling of Proteins in Biological Tissue Sections by MALDI Mass Spectrometry", Analytical Chemistry, Dec. 1, 1999, vol. 71, No. 23, pp. 5263-5270.

Cheng, Siew Bang et al., "Development of a Multichannel Microfluidic Analysis System Employing Affinity Capillary Electrophoresis for Immunoassay", Analytical Chemistry, Apr. 1, 2001, vol. 73, No. 7, pp. 1472-1479.

Crowther, John R., "ELISA, Theory and Practice" Meth. Mol. Biol., vol. 42, Humana Press, Totowa, NJ., pp. 35-62.

Deny, Yuzhong et al., "Chip-based Quantitative Capillary Electrophoresis/mass Spectrometry Determination of Drugs in Human Plasma", Analytical Chemistry Vol. 73, pp. 1432-1439.

Deo, Sapna K., et al., "An Innunoassay for Leu-enkephalin Based on a C-terminal Aequorin-peptide fusion", Analytical Chemistry, vol. 73, pp. 1903-1908.

Doucette, Alan et al., "Protein Concentration and Enzyme Digestion on Microbeads of MALDI-TOF Peptide Mass Mapping of Proteins for Dilute Solutions", Analytical Chemistry, Jul. 15, 2000, vol. 72, No. 1, pp. 3355-3362.

(Continued)

*Primary Examiner*—Heather G Calamita
(74) *Attorney, Agent, or Firm*—Elizabeth Arwine

(57) ABSTRACT

Immunoliposomes and use thereof in highly specific and sensitive nucleic acid amplification assays relying on amplification of specific nucleic acid sequences released from encapsulation within a liposome after a receptor on the liposome couples with a targeted analyte/antigen immobilized on a select surface. The immunoliposome nucleic acid amplification assay permits both quantitative and qualitative analyte detection.

11 Claims, 6 Drawing Sheets

OTHER PUBLICATIONS

Doyle, J. M., et al., "Electrochemical Sensors in Immunological Analysis", Plenum Press, New York, NY, pp. 87-102.

Egelhofer, V., Improvements protein identification by MALDI-TOF-MS Peptide mapping, Analytical Chemistry, Jul. 1, 2000, vol. 72, No. 13, pp. 2741-2750.

Feltus, Agatha et al., "Detection of Biotin in Individual Sea Urchin Oocytes Using a Bioluminescence Binding Assay", Analytical Chemistry, Apr. 1, 2001, vol. 73, No. 7, pp. 1403-1407.

Fraley, Robert et al., "Introduction of Liposome-encapsulated SV40 DNA into Cells", The Journal of Bilogical Chemistry, Nov. 10, 1980, vol. 255, No. 21, pp. 10431-10453.

Fry, David W., et al., "Rapid Separation of Low Molecular Weight Solutes from Liposomes Without Dilution", Academic Press Inc., 1978, pp. 809-815.

Gomori, G., "A Modification of the Colorimetric Phosphorus Determination for Use with the Photoelectric Colorimeter", The Journal of Laboratory and Clinical Medicine, pp. 955-960.

Heath, T.D., et al., "Covalent Attachment of Immunogobulins to Liposomes Via Glycosphingolipids", Biochimica et Biophysica Acta, 1981, vol. 640, pp. 66-81.

Hope, M. J., et al., "Production of Large Unilamellar Vesicles by a Rapid Extrusion Procedure. Characterization of Size Distribution, Trapped Volume and Ability to Maintain a Membrane Potential", Biochemica et Biophysica Acta, 1985, vol. 812, pp. 55-65.

Huang, Ching-Hsien, "Studies ofn Phosphatidylcholine Vesicles. Formation and Physical Characteristics", Biochemistry, Jan. 1969, vol. 8, No. 1, pp. 344-347.

Jones, Vivian W. et al., "Microminiaturized Immunoassays Using Atomic Force Microscopy and Compositionally Pattened Antigen Arrays", Analytical Chemistry, Apr. 1, 1998, vol. 70, No. 7, pp. 1233-1241.

Kung, Viola T. et al., "Synthesis of Carboxyacyl Derivatieves of Phosphatidylethanolamine and Use as an Efficient Method for Conjugation of Protein to Liposomes", Biochimica et Biphysica Acta, 1986, vol. 862, pp. 435-439.

Loyter, A. et al., "Fusion-Mediated Injection of SV40-DNA. Introduction of SV40-DNA into Tissue Culture Cells by the Use of DNA-Loaded Reconstituted Sendai Virus Envelopes", Experimental Cell Research, 1983, 143, pp. 415-425.

Martin, Francis J. et al., "Covalent Attachement of Proteins to Liposomes" in "Liposomes: a Practical Approach" (New, R.R.C., ed.) Oxford University Press, New York, NY, pp. 163-182.

Mason, J. T. et al., "Hydrodynamic Analysis of Egg Phosphatidylcholine Vesicles", Annals of the New York Academy of Sciences, Jun. 19, 1978, vol. 308, pp. 29-49.

Monroe, D., "Immunoassay Technology" (pal. S.B., ed.) Walter de Gruyter Co. Berlin, NY, pp. 167-187.

Nam, Jwa-Min et al., "Nanoparticle-Based Bio-Bar Codes for the Ultrasensitive Detection of Proteins", Science, Sep. 26, 2003, vol. 301, pp. 1884-1886.

Niemeyer, Christof M. et al., "Fluorometric Polymerase Chain Reaction (PCR) Enzyme-Linked Immunosorbent Assay for Quantification of Immuno-PCR Products in Microplates", Analytical Biochemistry, 1997, vol. 246, pp. 140-145.

Niemeyer, Christof M. et al., "Self-Assembly of DNA-Streptavidin Nanostructures and Their Use as Reagents in Immuno-PCR", Oct. 1999, vol. 27, No. 23, pp. 4553-4561.

New, R. R. C., "Characterization of Liposomes" in "Liposomes: A Practical Approach, Practical Approach", (New, R.R. C., ed.)Oxford University Press, New York, NY, 1990, pp. 105-161.

O'Leary, Timothy J. et al., "Use of Semiquantitative PCR to Assess Onset and Treatment of *Pneumocystis carinii* Infection in Rat Model", Journal of Clinical Microbiology, Mar. 1995, vol. 33, No. 3, pp. 718-724.

Payne, Nicholas I. et al., "Characterization of Proliposomes", Journal of Pharmaceutical Sciences, Apr. 1986, vol. 75, No. 4, pp. 330-333.

Qin, Qiu-Ping et al., "Development of Highly Fluorescent Detection Reagents for the Construction of Ultrasensitive Immunoassays", Analytical Chemistry, Apr. 1, 2001, vol. 73, No. 7, pp. 1521-1529.

Reid, Ann H., "Polymerase Chain Reaction" in "Advanced Laboratory Methods in Histology and Pathology", (mikel, U, ed.) American Registry of Pathology Publications Washington, DC, pp. 77-110.

Ruzicka, Viktor et al., "Immuno-PCR with a Commercially Available Avidin System", Science, Apr. 30, 1993, vol. 260, pp. 698-699.

Sano, Takeshi et al., "Immuno-PCR: Very Senitive Antigen Detection by Means of Specific Antibody-DNA Conjugates", Science, Oct. 2, 1992, vol. 258, pp. 120-122.

Sheng, Zong-Mei et al., "Rapid Screening for KIT Mutations by Capillary Electrophoresis", Clinical Chemistry, 2001, vol. 47, No. 7, pp. 1325-1326.

Singh, Anup K. et al., "Gangliosides as Receptors for Biological Toxins: Development of Sensitive Fluoroimmunoassays Using Ganglioside-Bearing Liposomes", Analytical Chemistry, Dec. 15, 2000, vol. 72, No. 24, pp. 6019-6024.

Smith, Ian C. P., et al., "Phosphorus-31 NMR of Phospholipids in Membranes", Academic Press, Inc. 1984, pp. 447-460.

Szoka, Jr., Francis et al., "Procedure for Preparation of Liposomes with Large Internal Aqueous Space and High Capture by Reverse-phase Evaporation", Pro.Natl. Acad. Sci., Sep. 1978, vol. 75, No. 9, pp. 4194-4198.

Szoka, Jr., Francis et al., "Comparative Properties and Methods of Preparation of Lipid Vesicles (Liposomes)", Ann. Rev. Biophys. Bioeng., 1980, vol. 9, pp. 467-508.

Tanabe, Tetsuya et al., Fluorescent Cyclodextrin Immobilized on a Cellulose Membrane as a Chemosensor System for Detecting Molecules, Analytical Chemistry, Apr. 15, 2001, vol. 73, No. 8, pp. 1877-1880.

Wang, Joseph et al., "Capillary Electrophoresis Microchips for Separation and Detectionof Organophospate Nerve Agents", Analytical Chemistry, Apr. 15, 2001, vol. 73, No. 8, pp. 1804-1808.

Wong, W. M. et al., "Genomic Sequence of a Sprague-Dawley rat β-globin gene", Nucleic Acids Research, 1988, vol. 16, No. 5, p. 2342-2348.

Wu, H. C. et al, "Detection of Clostridium Botulinum Neurotoxin in Type A Using Immuno-PCR", Letters in Applied Microbiology, 2001, vol. 31, pp. 321-325.

Young, Karen K. Y. et al., "Detection of Hepatitis C Virus RNA by a Combined Reverse Transcription-Polymerase Chain Reaction Assay", Journal of Clinical Microbiology, Apr. 1993, vol. 31, No. 4, pp. 882-886.

Huang et al., Biotechniques, vol. 20:1012-1020, 1996.

Cao et al., The Lancet, vol. 356:1002-1003, 2000.

\* cited by examiner

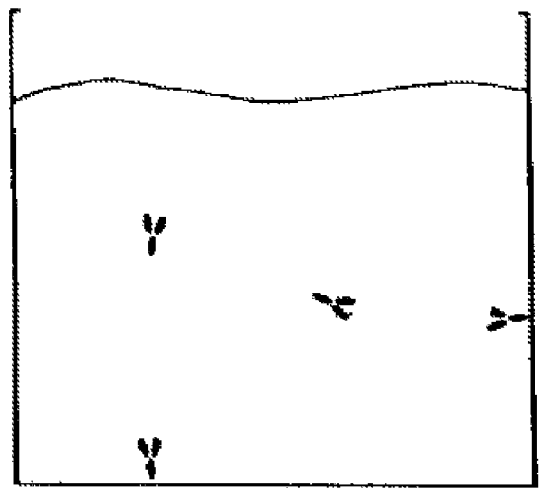
FIG. 1
FIG. 2
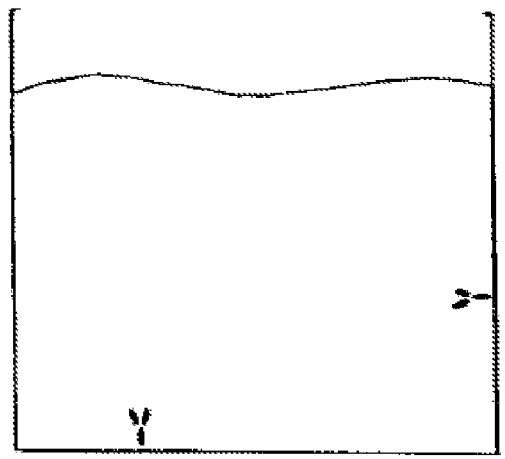
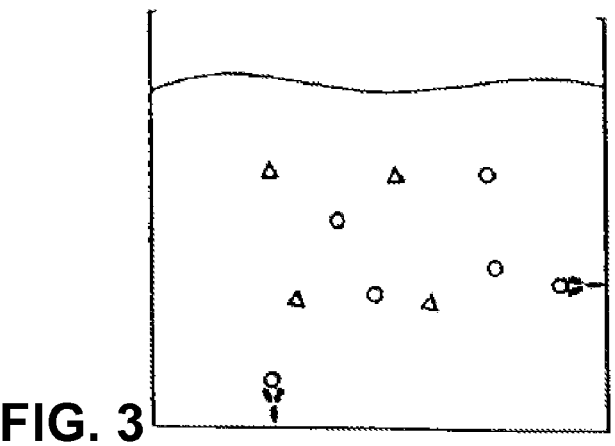
FIG. 3

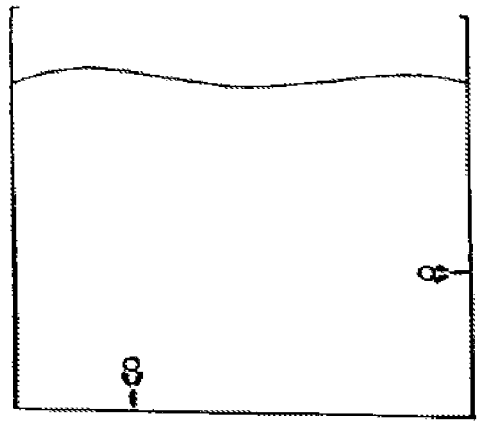
FIG. 4
FIG. 5
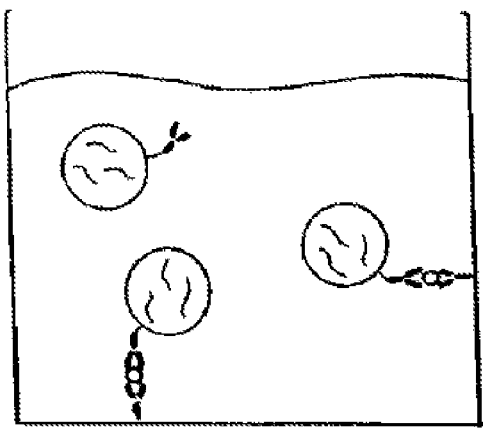
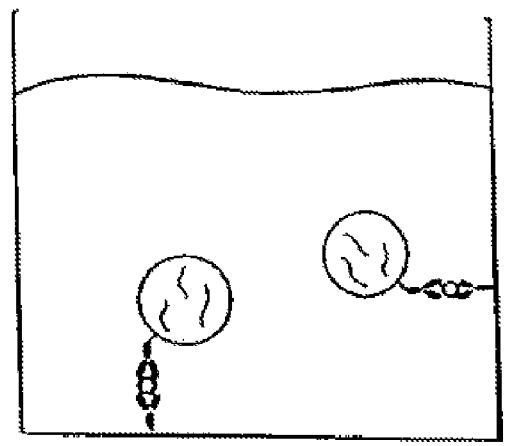
FIG. 6

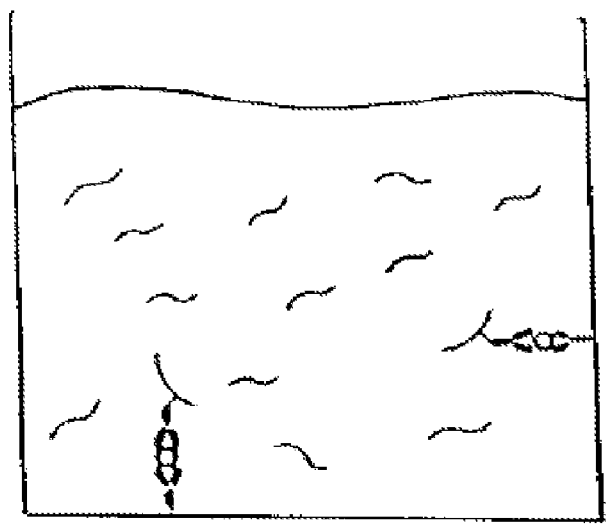
FIG. 7
FIG. 8
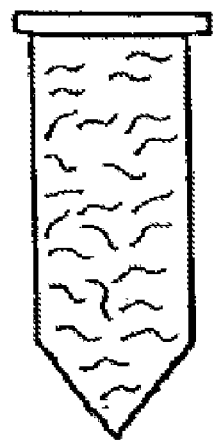
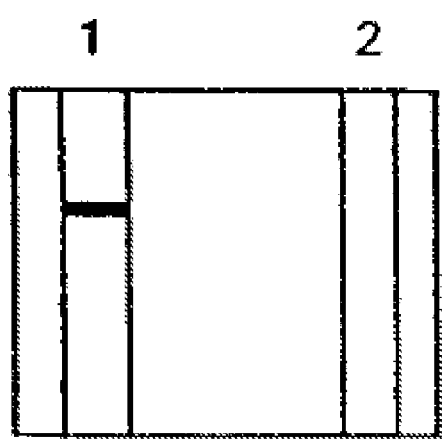
FIG. 9

IMMUNOLIPOSOME-NUCLEIC ACID AMPLIFICATION (ILNAA) ASSAY

This application is a divisional application of U.S. Ser. No. 10/759,099 filed in the U.S. Patent and Trademark Office on Jan. 20, 2004, now U.S. Pat. No. 7,582,430, the entirety of which is incorporated herein by reference.

I. FIELD OF THE INVENTION

This invention relates to a new assay system and method for detecting extremely small quantities (as few as 10-1000 molecules) of compounds for which specific receptors, such as antibodies, exist. The invention is referred to as an immunoliposome-nucleic acid amplification (ILNAA) assay method.

II. BACKGROUND OF THE INVENTION

The early and rapid detection of biological toxins is critically important to the protection of security personnel deployed in hostile situations or in instances of domestic terrorism. Biological toxins, such as botulinum toxin, are lethal at very low concentrations, which necessitates detection measures that are both highly specific and extremely sensitive. There are a multitude of scenarios that may require the ability to detect biological toxins at sub-attomolar ($10^{-18}$M) concentrations or even at levels approaching a few molecules. Foremost, early detection of the use by, for example, terrorists, of biological toxins will allow time for countermeasures, thus decreasing the likelihood of death or injury due to exposure. Civil and military investigative activities require attempts to identify sites of manufacture or storage of biological toxins by soil or water sampling at considerable distances from the suspected site. Such activities may also include attempts to identify former storage sites for biological weapons after the material has been moved and even after attempted sterilization of the site. The military is frequently called upon to clean up storage sites for biological weapons, which requires the ability to survey for residual contamination. Finally, terrorist acts involving biological toxins will frequently require examination of trace forensic evidence for the presence of toxins. All of these examples point to the need for rapid and reliable tests for toxins that are highly specific, but also sufficiently sensitive to detect the target toxin down to the level of a few molecules. In summary, there exists a substantial need for detection capabilities of biological toxins, infectious bacteria and viruses, chemical warfare agents, poisons and other chemical toxins, explosive compounds, and trace forensic evidence.

Presently, cutting-edge techniques employed for the selective high sensitivity detection of protein antigens are antibody-based immunoassays (including "biochip" devices), mass spectrometry, DNA-amplification methods, and nanotechnology techniques. Each of these techniques suffers from drawbacks and problems. Immunoassay methods, such as enzyme-linked immunosorbent assays (ELISAs), employ antibodies directed against a protein antigen to form a highly selective detection method. Assay sensitivity is produced by linking a moiety to the detecting antibody that is capable of some form of signal amplification. However, even under ideal circumstances, ELISA's suffer from detection limits, which are restricted to the nanomolar (nM) to femtomolar (fM) concentration range.

Biochip methods for detecting proteins are a variation of the immunoassay method where antibodies are attached to a membrane in a pattern that can be ready by an optical scanner. The signal amplification methods employed are the same as those for other immunoassays and thus the detection limit is limited to the picomolar level with practical detection limits in the micromolar ($10^{-6}$M) to nanomolar range (Wang et al., 2001; Cheng et al., 2001; Tanabe et al., 2001; Deng et al., 2001). It is important to appreciate that the greatest advantage of biochip technology is the ability to screen for many antigens at one time (high throughput) rather than high sensitivity for any one antigen.

Nanomolar ($10^{-9}$M) sensitivity regularly can be achieved with single-shell closed-sphere bilayers (liposomes) with diameters of ~100 nm containing up to 25,000 fluorescent probes imbedded in each bilayer. Such liposomes can be covalently linked to antibodies and used as the basis of a fluorescence liposome detection method. Since each binding event involves one liposome, signal amplifications of up to 25,000:1 are possible. (Singh et al., 2000).

Greater detection sensitivity can be achieved using amperometric enzyme detection. Enzymes, such as horseradish peroxidase, are linked to the detecting antibody and the product of the enzyme reaction is detected amperometrically through its precipitation on an electrode surface. The amplified electronic transduction of antigen-antibody binding events that results from the activity of the enzyme, forms the basis of the signal amplification (bioelectronic device). This technique permits detection of antigen concentration down to the picomolar ($10^{-12}$M) level (Alfonta et al., 2001; Doyle et al., 1987). Another technique proving ~10 femtomolar ($10^{-15}$M) sensitivity involves the use of fluorescence detection based on highly fluorescent Europium chelates. The chelates are linked to antibodies for detection of antigen-antibody binding. Recent literature reports that heavily labelled Europium chelates polymers (up to 110 total) may be covalently linked to streptavidin based conjugates to detect near femtomolar amounts of prostate-specific antigen (Qin et al., 2001). However, in order to limit background fluorescence to acceptable levels, only small sample volumes (10-20 microliters) can be used for this detection method.

Another approach provides even greater detection sensitivity. When antibodies are coupled to a luminescent protein, such as aequorin from the jellyfish *Aequorea victora*, the luminescent detection of the bound aequorin yields a detection limit down to the femtomolar ($10^{-15}$M) level due to the intense bioluminescence of aequorin (Deo and Daunert, 2001; Feltus, et al., 2001). Attomolar ($10^{-18}$M) concentrations of antigen have been detected with aequorin luminescence, but only by employing a complex optic and detector scheme and by using nanoliter sample volumes (Feltus et al., 2001) to limit the background signal.

Taken as a whole, the immunoassay methods offer outstanding selectivity due to the specificity of the antigen-antibody interaction, but offer only modest sensitivity that is limited in practice to the nanomolar to picomolar concentration range. Higher sensitivities down to the femtomolar range (or the attomolar range for aequorin luminescence) are achievable only with nanoliter sample volumes (in order to limit the protein autofluorescence background signal) and the application of sophisticated optical detection systems that are impractical for field deployable devices.

Advances in mass spectrometric methods, in particular matrix-assisted laser desorption/ionization time-of-flight (MALDI-TOF) mass spectrometry, have taken a leading role in the analysis of peptides and proteins (Chaurand et al., 1999). Detection of proteins in biological fluids at sub-femtomolar concentrations is now possible. However, it is not currently possible to uniquely identify a protein, such as a biological toxin, through its mono-ionic species in the MALDI-TOF mass spectrum. As a result, protein identification is achieved by observing the mass spectra of the fragments that result from the proteolytic digestion (typically with trypsin) of the protein and then comparing this spectrum with a library database of known proteins. This process is referred to as protein mapping (Egelhofer et al., 2000). Unfortunately, the kinetics of the proteolytic digestion step limits the lowest practical protein concentration to the micromolar range (Doucette et al., 2000). Recent advances using immobilized tryspin and preproteolytic sample concentration have extended the protein concentration detection limit to the nanomolar level (Doucette et al., 2000). Despite these advances, mass spectrometry clearly lacks both the specificity and sensitivity required for a high sensitivity assay system to detect proteins at the sub-attomolar concentration level.

The most sensitive biological signal amplification scheme ever developed, polymerase chain reaction (PCR), is limited to nucleic acid amplification and cannot directly be used to detect proteins. Indeed, PCR based techniques have already been employed for the high sensitivity detection of organisms that produce biological toxins or disease hazards through PCR amplification of their genomic DNA or RNA (Young et al., 1993). Recently, a new technique combining a hybrid protein assay coupling the use of antibodies directed against proteins and PCR referred to as "immuno-PCR," has been developed to detect proteins.

Current immuno-PCR techniques employ one of two approaches for coupling amplification substrates (DNA fragments) to antibodies. Direct covalent attachment of the amplification substrate to the antibody of interest is discussed in Wu et al. (2001). This method exploits the terminal phosphate moiety of the amplification substrate, or an amplification substrate modified to contain and amine group, as the basis for the covalent coupling of the amplification substrate to the antibody. Indirect non-covalent attachment of biotinylated amplification substrate and biotinylated antibody to a common streptavidin molecule is described in Sano et al. (1992) and Niemeyer et al. (1997).

In these assays the target protein antigen is immobilized on a substrate (such as a microtiter plate well) and the antibody-DNA complex is allowed to bind to the immobilized antigen. This is followed by the removal of unbound antibody-DNA complex by extensive rinsing. The bound antigen is then detected through the PCR amplification of the amplification substrates attached to the antibody with visualization achieved by gel electrophoresis or a real-time PCR assay. These assays have been employed to achieve detection limits of roughly 6,000,000 (Wu et al., 2001) to 60,000 (Niemeyer et al., 1997) molecules.

Immuno-PCR methods present several difficulties, particularly for field application, as for example, in the military. The detection sensitivity is still relatively low due to extreme potency of some biotoxic agents such as Botulinum or tetanus toxin, detection sensitivity down to the 10-100 molecule level is necessary. The Immuno-PCR methods described above link a single (or at most four) amplification substrates to each antibody. This severely limits the ability of these methods to detect very low copy numbers of antigens (10-100) as detection of only a few copies of the target DNA molecule by PCR is often difficult or impossible. Many samples contain Taq polymerase inhibitors that can inhibit or prevent the replication of low numbers of starting DNA molecules. Furthermore, particularly when in the field, contamination of samples with extraneous DNA is a critical concern for samples with low target DNA concentrations. Finally, even where amplification is successful, it entails a large and time-consuming number of amplification cycles to produce enough DNA to allow for reliable detection of the amplified product.

Recently, three nanotechnology based protein assay methods have been introduced. The first uses atomic force microscopy to perform micro-miniaturized immunoassays on compositionally patterned antibody arrays (Jones et al., 1998). This technique can theoretically detect and identify single antigens based upon the increase in topological height when an antigen binds to an antibody at a specific location in the array. Although highly sensitive and specific, this method requires complex nanofabrication techniques and employs sensitive instrumentation not compatible with use in the field. The other assay methods employ the self-assembly of DNA-streptavidin nanostructures (Niemeyer et al., 1999) or antibody-labeled magnetic beads and sub-micron sized gold particles labelled with antibodies and DNA segments (Nam et al., 2003) for performing immuno-PCR. Although both techniques can detect antigens down to the level of 10-100 molecules, both require sophisticated nanofabrication and detection techniques beyond the capability of most laboratories and researchers.

In summary, none of the current cutting-edge methodologies discussed above are well suited to the development of a highly selective ultra-sensitive assay system for detecting biological toxin hazards in military deployment situations.

Notwithstanding the usefulness of the above-described methods, a need still exists for an ideal assay that would employ antibodies (or other specific receptors) for detection, due to their very high selectivity for proteins, and also employ some form of nucleic acid amplification as a highly sensitive detection method. In order to extend the detection limit down to 10-100 molecules of antigen a method is required to overcome the limitations associated with low initial copy numbers of amplification substrates that severely limit the current immuno-PCR methods. This is achieved in our ILNAA assay method by attaching antibodies (or other specific receptors) to closed-shell liposomes of about 100 nm in diameter that encapsulate 50-1000 amplification substrates inside each liposome. In this way each antibody-binding event is associated with 50-1000 amplification substrates rather than one amplification substrate as is the case for the current immuno-PCR methods. This approach overcomes the difficulty in initiating the amplification reaction starting with just a few amplification substrates. For example, for 10 bound antigens there would be only 10 amplification substrates with which to initiate the PCR reaction with the current immuno-PCR methods, but 500 to 10,000 with our ILNAA assay method. This improvement in the number of amplification substrates per binding event also serves to proportionally reduce the problems associated with background DNA or RNA contamination, which improves proportionally with the initial number of amplification substrates present at the start of PCR or RT-PCR. Finally, our ILNAA assay method presents a unique approach for further reducing the background nucleic acid contamination. In our assay the amplification substrates are encapsulated inside closed-shell liposomes and, as such, are sequestered from the rest of the assay solution.

This allows for the addition of DNase or RNase to the assay solution as a means of degrading any background DNA or RNA present that could be amplified by the nucleic acid amplification step and present a false positive, reducing the sensitivity and reproducibility of the assay. The enzyme can be heat deactivated prior to the rupture of the liposomes so that the released amplification substrates are the only source of nucleic acid capable of being amplified. In the current immuno-PCR methods the amplification substrates are exposed to the bulk assay solution making DNase reduction of background DNA impossible as the amplification substrates themselves would also be degraded. For the above reasons our ILNAA assay method represents a significant enhancement over existing high-sensitivity assay systems and solves the problems associated with the highly selective detection of antigens at extremely low copy numbers.

III. SUMMARY OF THE INVENTION

Accordingly, it is an object of the present invention to overcome the problems associated with the prior art.

It is another object of this invention to provide immunoliposome structures and methods for use in analyte detection.

Another object of this invention is to provide a highly specific and extremely sensitive analyte detection method.

A further object of this invention is to provide an immunoliposome nucleic acid amplification assay method permitting detection of any selected analyte, including toxins, infectious agents, poisons, explosives, trace forensic evidence, and the like, at extremely small quantities (as few as $10-10^3$ molecules)

Still another object of this invention is to provide an elegant assay technique that is employable both in the laboratory and the field.

Still another object of this invention is to provide an assay capable of enhanced specific binding while minimizing background contamination and false readings.

Yet another object of this invention is to provide a highly selective and sensitive detection assay that uses conventional equipment.

Many of these objects are met by a method for immunoliposome-nucleic acid amplification assay, comprising the steps of; encapsulating a plurality of identical nucleic acid segments within liposomal bilayers, associating selected receptors to said liposomal bilayers, exposing said selected receptors to immobilized target analyte which bind to said liposomal bilayer associated selected receptors, removing unbound liposomal bilayers, lysing said bound liposomal bilayers to release said nucleic acid segments, amplifying said released nucleic acid segments, and detecting the released nucleic acids.

Certain objectives are met by an immunoliposome, comprising a plurality of nucleic acid oligomers having identical sequences selected to correspond to a target antigen, an encapsulating liposome bilayer and receptors coupled to said bilayer where said receptors are selected to bind with said target antigen.

The inventive assay method of the invention, referred herein as ILNAA provides a highly specific and extremely sensitive assay to detect toxins used, for example, in biological warfare, poison attacks by terrorists, etc. The ILNAA assay method is extremely versatile so it has more general application in forensic and clinical detection of virtually any compound for which a specific receptor exists.

Generally, this invention is a method for detecting extremely small quantities (as few as 10-1000 molecules) of compounds for which specific receptors (such as antibodies) exist. The receptors are coupled to the outer surface of closed-shell bilayer membranes (liposomes) that are formed in such a way that they encapsulate 50-1000 copies of short DNA or RNA segments (amplification substrates) that are capable of being amplified by the polymerase chain reaction (PCR) or any other nucleic acid amplification technology (such as RT-PCR, bDNA or Q-beta-replicase). As the receptors used are typically antibodies these structures are referred to as "immunoliposomes", which are depicted in FIG. 10. The target antigen is immobilized on a substrate (typically inside the wells of a microtiter plate) and unbound antigen is removed by rinsing. The immunoliposomes are then added to the solution and allowed to bind to the target antigen and any unbound immunoliposomes are subsequently removed by rinsing. The remaining specifically bound immunoliposomes are ruptured by the addition of a non-ionic detergent, which causes them to release their amplification substrates into the bulk solution. The amplification substrates are then amplified by PCR or RTPCR and detected by gel or capillary electrophoresis. Alternately, the released amplification substrates can be amplified and detected by a real-time (homogeneous) PCR/RT-PCR assay or any other coupled nucleic acid amplification/detection technology (such as bDNA or Q-betareplicase).

The invention herein offers significant advantages over the current immuno-PCR methods. For example, the ILNAA contemplates the encapsulation of the amplification substrates into liposomes and providing the ability to use DNase or RNase to reduce background DNA or RNA contamination. The invention envisions highly adaptable chemistry for linking antibodies or other specific receptor molecules to the liposomal surface and for reducing non-specific binding.

Practically, the invention envisions application in a wide range of clinical and medical fields. The invention can accommodate high-throughput detection of specific proteins or nucleic acid sequences in microchip technologies. ILNAA is applicable for detection of normal or pathogenic proteins, carbohydrates, glycolipids, and gangliosides of all kinds even in extremely small (sub-attomolar) quantities. The invention can be used for detection of the presence of targets ranging from specific DNA and RNA sequences, pathogens (viruses and bacteria), biological membrane receptors, cancer-specific soluble biological markers, tumor cell-surface markers, and hormones to immune system cells and fragments and minor cell components in larger cellular populations. The invention can also be used to detect the spatial localization of any of the above in fresh or fixed tissue sections.

The invention also finds use in such diverse endeavors as environmental and industrial applications such as detection of environmental toxins and pollutants in soil, water, and air samples, detection of specific target ionic species, detection of trace contaminants in manufacturing processes or equipment, detection of pathogens and toxins in fresh and processed foods.

General discrete aspects of this invention are now discussed.

A. Encapsulation of Amplification Substrates into Liposomes

In ILNAA amplification substrates preferably are in the form of immunoliposomes; encapsulated closed-shell liposomes covalently linked to the antibody of interest. The immunoliposomes are allowed to bind to an immobilized antigen (typically in an microtiter plate well) and any unbound immunoliposomes are removed by extensive rinsing. The remaining specifically bound immunoliposomes are then ruptured with a non-ionic detergent and the amplification substrates are liberated into the bulk solution. The liberated amplification substrates are amplified by PCR (or RT-PCR) and detected by gel electrophoresis, capillary electrophoresis, or a real-time amplification method, such as a Taqman® assay.

Among the advantages of the present invention and the disclosed liposome encapsulating amplification technique over conventional direct or indirect attachment strategies used in the current immuno-PCR methods is that the invention permits encapsulation of a substantial number of amplification substrates per liposome, e.g., 50-1000. Thus each antibody-binding event is associated with, for example, 50 to 1000 amplification substrates rather than 1 amplification substrate as is the case for the current immuno-PCR techniques. Consequently, the present invention enjoys significantly enhanced sensitivity, as a 50 to 1,000-fold enhancement in the case of the exemplary 50-1000 substrate per liposome example. Additionally, where samples contain amplification inhibitors, e.g., Taq polymerase inhibitors, PCR amplification of low copy numbers of target DNA sequences may be rendered difficult or impossible. The present invention overcomes this problem by significantly increasing the number of amplification substrates per binding event.

Correspondingly, the present invention mitigates the impact of sample contamination. For example, in high-sensitivity assays employing PCR or RT-PCR, contamination of the solutions or materials employed with background DNA or RNA is a critical issue. In general, the lower the concentration of target nucleic acid to be amplified the greater the sensitivity of the PCR or RT-PCR assay to such background contamination. Because the invention increases the number of amplification substrates per binding event, the susceptibility of the assay to background nucleic acid interference is proportionally reduced.

The invention enhances processing speed. Increasing the number of amplification substrates per binding event by a factor of 50 to 1,000 significantly reduces the number of PCR or RT-PCR amplification cycles required to produce a detectable level of product. This will result in substantial savings in time and cost associated with use of the invention.

The assay of this invention also can be adapted readily to screen/test for several compounds at one time. Each specific antibody (or other specific receptor molecule) can be linked to liposomes that contain amplification substrates of a unique nucleotide length. Following PCR or RT-PCR, a series of distinct nucleic acid bands will appear upon gel or capillary electrophoresis of the sample that correlate with the specific antigens associated with the amplification substrates of those lengths. This approach is possible with the covalent attachment method of Wu et al., 2001, but not with the biotin-based non-covalent attachment methods of Sano et al., 1992 or Niemeyer et al., 1997.

B. Ability to use DNase or RNase to Reduce Background DNA or RNA Contamination The inventive ILNAA assay method provides for further reductions in the effects of background DNA or RNA contamination and the corresponding adverse impact on sensitivity and reproducibility of the assay. In the preferred embodiment, the amplification substrates are encapsulated within closed-shell liposomes and, as such, are sequestered from the rest of the assay solution. This allows for the a further intermediate step of adding DNase or RNase to the assay solution to degrade background DNA or RNA that could otherwise present a false positive upon amplification by the PCR (RT-PCR) step. Prior to the rupture of the liposomes, the lysing enzyme can be heat deactivated so that the released amplification substrates provide the only source of nucleic acid capable of being amplified. Contrary to conventional immuno-PCR methods, the amplification substrates are exposed to the bulk assay solution making DNase reduction of background DNA impossible as the amplification substrates themselves would also be degraded.

C. Surface Attachment Chemistry

Integral membrane proteins are important specific receptors for a variety of viruses, bacteria, toxins, chemical warfare agents, hormones, proteins, and cancer markers. However, integral membrane proteins require a lipid environment in order to maintain their native properties. The invention differs from current immuno-PCR methods which are limited in the chemistry that can be used to covalently attach the amplification substrate to the antibody (or other specific receptor molecule) of interest.

The present invention facilitates incorporating integral membrane proteins directly into the liposomes used to encapsulate the amplification substrates. Covalent attachment of antibodies to DNA is limited to the natural phosphate group or requires the costly introduction of modified nucleotide bases into the amplification substrate through sequence-specific DNA synthesis, as for example, in streptavidin-biotin procedures which require the costly introduction of biotin into the amplification substrate.

Contrarily, in the method of the present invention, the antibody (or other specific receptor molecule) of interest is attached to the extravesicular surface of the liposome. The present invention, at once, enhances the range of attachment strategy choices thereby permitting selection of simpler and less costly attachment strategies. For example, an antibody (or other specific receptor molecule) of interest can be securely anchored to the extravesicular surface of the liposome through covalent attachment to a variety of long-chain-length hydrocarbons (12-24 carbons) that can partition into the hydrophobic core of the bilayer. Long-chain-length carboxylic acids, amines, thiols, alcohols, aldehydes, nitriles, amides, and halides are usable as such hydrocarbon anchors. Another approach involves covalently attaching the antibody to glycolipids and phospholipids, such as phosphatidylethanolamine or phosphatidylserine, through their functional groups.

Molecules to be used as specific receptors that are charged can be electrostatically coupled to the extravesicular surface of the liposome by introducing charged lipids (such as sterylamine (+ charge) or phosphatidylserine (− charge)) into the liposomal bilayer. Electrostatic coupling can then be achieved by matching opposite charges or by coupling like charges through the use of divalent cations. An example of the latter would be the coupling of a negatively charged detection molecule to phosphatidylserine through a calcium bridge.

One further example provided here involves the use of naturally occurring membrane receptors for hormones, toxins, drugs, pathogens, or other antigens of interest. These moieties can be incorporated into the liposomal bilayer through electrostatic coupling (surface receptors) or by direct incorporation as integral membrane proteins, into the liposomes as during formation thereof.

The availability of the wide range of attachment methods clearly distinguishes the invention herein from current immuno-PCR methods. As should be apparent to the skilled artisan upon review of the present specification, the invention contemplates using any conventional coupling strategies, attaching a vast range of antibodies/receptor molecules to a selected extravesicular liposomal surface.

D. Approaches to Reduce Non-Specific Binding

ILNAA assay method offers a variety of approaches to limit non-specific binding by modifying the properties of the immunoliposome itself in addition to modifications of the immobilizing substrate. This type of approach is not possible with the current immuno-PCR methods. Non-specific binding of an antibody detection complex reduces the sensitivity and accuracy of conventional immunoassays. Non-specific binding becomes a progressively more pronounced with decreasing concentrations of antigen, a significant problem with any high-sensitivity immunoassay. No method is known for modifying the antibody-DNA complex (or antibody streptavidin-biotin complex) directly to inhibit non-specific binding except to mask binding sites on the immobilizing substrate with long DNA strands or with proteins, such as BSA.

Two examples for reducing non-specific binding to liposomes according to this invention are now provided. The first technique concerns varying the lipid composition of the bilayer to alter the polarity and charge of the liposomal surface. The selection of specific lipids for incorporation into the bilayer, may produce a surface exhibiting neutral, negative, or positive charged characteristics. Moreover, the charge density of the surface can be varied in liposomes formulated to contain a net charge. For neutral bilayers, the lipid composition can be altered to vary the polarity of the surface. For example, the inclusion of glycolipids will increase the polarity of the liposomal surface, while the inclusion of neutral phospholipids will decrease the polarity of the surface.

Another technique, particularly applicable for use in studies that use liposomes for drug delivery in vivo, involves the attachment of certain polymers, such as polyethylene glycol (PEG), to the liposome's extravesicular surface. The polymers serve to reduce the "stickiness" of liposomes in vivo and, correspondingly, increase their retention time in circulation. Such approaches can be tried in an attempt to reduce non-specific binding in the immunoassay. The liposomes could also be coated with charged or perfluorinated polymers in an attempt to reduce non-specific binding.

In summary, numerous methods for modifying the properties of the immunoliposome are possible in an attempt to minimize non-specific binding in a given assay. Such techniques are not available to current immuno-PCR assay methods.

DEFINITIONS

"Amplicon" as used herein, means an amplification substrate and may be a gene fragment/nucleic acid sequence that serves as an agent to identify, detect and even quantify the amount of a target analyte, e.g., biological toxin, poison, etc. present in a sample.

"Amplification substrate" as used herein, means a short DNA or RNA segment that can be amplified by PCR, RT-PCR, or any other nucleic acid amplification process, such as bDNA or Q-beta-replicase. As the amplification substrate serves only as a signal amplification mechanism the choice of the amplification substrate to use is not critical. However, certain guidelines are that the amplification substrate is short (25-100 base pairs) to maximize the number of amplification substrates that can be encapsulated per liposome and that the amplification substrate is not likely to be found in the sample being analyzed in order to reduce the likelihood of false positives.

"Coupling method" refers to the functionality/process whereby the chosen specific receptor molecule is attached to (or incorporated into) the outer surface of the encapsulating structure. The coupling method to be employed will depend upon the chemical properties of both the specific receptor molecule chosen and the encapsulating structure to be employed. The coupling can be either covalent or non-covalent in nature.

"Immunoliposome" as used herein, in the preferred form is the combination of encapsulating amplification substrates into closed-shell liposomes, which are then covalently or non-covalently linked to the antibody (or other specific receptor) of interest.

In the context of this invention "liposome" refers to any structure that can (a) encapsulate amplification substrates thereby sequestering them from the chemical environment outside of the structure, (b) allow for the attachment of the chosen specific receptor molecule to the outer surface of the structure, and (c) allow for the release (by any method) of the encapsulated amplification substrates into the bulk solution for nucleic acid amplification and detection after specific binding to the target compound has been achieved. While describing closed-shell phospholipid bilayers as the encapsulating structure, the word "liposome" is intended to contemplate other suitable encapsulating structures.

"Nucleic acid amplification" as used herein means any known method by which the chosen amplification substrate is reproduced for detection. The amplification method to be employed (such as PCR or RT-PCR) will depend upon the amplification substrate that has been chosen, the analyte of interest, and the conditions under which the assay is to be performed. In some cases, the amplification and detection methods may be highly coupled (such as bDNA and Q-beta replicase methods).

"Nucleic acid detection" method as used in this specification, means any known process whereby an amplified nucleic acid product is detected to ascertain the presence and/or quantity of the compound being assayed. The nucleic acid detection method would include any and all methods that can be used to detect and/or quantitative DNA or RNA and includes, but is not limited to, gel electrophoresis, capillary electrophoresis, spectrophotometric or fluorometric assays with nucleic acid specific dyes, and secondary methods to detect nucleic acids such as labeled antibodies directed against modified nucleic acids. Also included are any real-time quantitative PCR (RT-PCR) methods such as Taqman® or Lightcycler® assays, and bDNA and Q-beta replicase methods.

"Specific receptor molecule" means a molecule that serves to unambiguously identify a compound (or class of compounds) by tightly and specifically binding to (or reacting with) that compound and no other. The choice of the specific receptor molecule is dependent upon the compound that one desires to detect. In most cases this will be a protein and the specific receptor will be a monoclonal or polyclonal antibody directed against that protein. However, other specific receptor molecules that can be employed include (but are not limited to) gangliosides, glycolipids, biological membrane receptors, molecules that bind specific ions, and compounds designed to bind specifically to (or react specifically with) chemical warfare agents, explosives, poisons, or any other target molecule. Also included are soluble proteins, dyes, and DNA or RNA probes designed to bind to specific nucleic acid target sequences.

As used herein "connected" includes physical, whether direct or indirect, hardwired or wireless, or any operationally functional connection.

As used herein "substantially" is a relative modifier intended to indicate permissible variation from the characteristic so modified. It is not intended to be limited to the absolute value or characteristic which it modifies but rather approaching or approximating such a physical or functional characteristic.

TECHNICAL REFERENCES

Alfonta, L., Singh, A. K., and Willner, I. (2001) "Liposomes labeled with biotin and horseradish peroxidase: a probe for the enhanced amplification of antigen-antibody or oligonucleotide-DNA sensing processes by the precipitation of an insoluble product on the electrode" *Anal. Chem.* 73, 91-102.

Bailey, A. L. and Sullivan, S. M. (2000) "Efficient encapsulation of DNA plasmids in small neutral liposomes induced by ethanol and calcium" *Biochimica et Biophysica Acta* 1468, 239-252.

Bridges, M. A., McErlane, K. M., Kwong, E., Katz, S., and Appelgarth, D. A. (1986) "Fluorometric determination of nanogram quantities of protein in small samples: application to calcium-transport adenosine triphosphatase" *Clin, Chim. Acta* 157, 73-79.

Chaurand, P., Stoeckli, M., and Caprioli, R. M. (1999) "Direct profiling of proteins in biological tissue sections by MALDI mass spectrometry" *Anal. Chem.* 71, 5263-5270.

Cheng, S. B., Skinner, C. D., Taylor, J., Attiya, S., Lee, W. E., Picelli, G., and Harrison, D. J. (2001) "Development of a multichannel microfluidic analysis system employing affinity capillary electrophoresis immunoassay" *Anal. Chem.* 73, 1472-1479.

Crowther, J. R. (1995) "ELISA, Theory and Practice" *Meth. Mol. Biol.* 42, Humana Press, Totowa, N.J., pp 35-62.

Deng, Y., Zhang, H., and Henion, J. (2001) "Chip-based quantitative capillary electrophoresis/mass spectrometry determination of drugs in human plasma" *Anal. Chem.* 73, 1432-1439.

Deo, S. K. and Daunert, S. (2001) "An immunoassay for Leu-enkephalin based on a C-terminal aequorin-peptide fusion" *Anal. Chem.* 73, 1903-1908.

Doucette, A., Craft, D., and Li, L. (2000) "Protein concentration and enzyme digestion on microbeads for MALDI-TOF peptides mass mapping of proteins from dilute solutions" *Anal. Chem.* 72, 3355-3362.

Doyle, J. M., Wehmeyer, K. R., Heineman, W. R., and Halsall, H. B. (1987) in "Electrochemical Sensors in Immunological Analysis" (Ngo, T. T., ed.) Plenum Press, New York, N.Y., pp 87-102.

Egelhofer, V., Bussow, K., Luebbert, C., Lehrach. H., and Nordhoff, E. (2000) "Improvements in protein identification by MALDI-TOF-MS peptide mapping" *Anal. Chem.* 72, 2741-2750.

Feltus, A., Grosvenor, A. L., Conover, R. C., Anderson, K. W., and Daunert, S. (2001) "Detection of biotin in individual sea urchin oocytes using a bioluminescence binding assay" *Anal. Chem.* 73, 1403-1407.

Fraley, R., Subramani, S., Berg, P., and Papahadjopoulos, D. (1980) "Introduction of liposome-encapsulated SV40 DNA into cells" *J. Biol. Chem.* 255, 10431-10435.

Fry, D. W., White, J. C., Goldman, I. D. (1978) "Rapid separation of low molecular weight solutes from liposomes without dilution" *Anal. Biochem.* 90, 809-815.

Gomori, G. (1942) "A Modification of the Colorimetric Phosphorus Determination for Use with the Photoelectric Colorimeter" *J. Lab. Clin. Med.* 27, 955-960.

Heath, T. D., Macher, B. A., and Papahadjopoulos, D. (1981) "Covalent attachment of immunoglobulins to liposomes via glycosphingolipids" *Biochimica et Biophysica Acta* 640, 66-81.

Hope, M. J., Bally, M. B., Webb, G., and Cullis, P. R. (1985) "Production of large unilamellar vesicles by a rapid extrusion procedure. Characterization of size distribution, trapped volume and ability to maintain a membrane potential" *Biochimica et Biophysica Acta* 812, 55-65.

Huang, C. (1969) "Studies on phosphatidylcholine vesicles, Formation and physical characteristics" *Biochemistry* 8, 344-352.

Jones, V. W., Kenseth, J. R., Porter, M. D., Mosher, C. L., and Henderson, E. (1998) "Microminiaturized immunoassays using atomic force microscopy and compositionally patterned antigen arrays" *Anal. Chem.* 70, 1233-1241.

Kung, V. T. and Redemann, C. T. (1986) "Synthesis of carboxyacyl derivatives of phosphatidylethanolamine and use as an efficient method for conjugation of protein to liposomes" *Biochimica et Biophysica Acta* 862, 435-439.

Loyter, A., Vainstein, A., Graessmann, M., and Graessman, A. (1983) "Fusion-mediated injection of SV40-DNA. Introduction of SV40-DNA into tissue culture cells by the use of DNA-loaded reconstituted Sendai virus envelopes" *Exp. Cell Res.* 143, 415-425.

Martin, F. J., Heath, T. D., and New, R. R. C. (1990) "Covalent attachment of proteins to liposomes" in "Liposomes: a Practical Approach" (New, R. R. C., ed.) Oxford University Press, New York, N.Y., pp 163-182.

Mason, J. T. and Huang, C. (1978) "Hydrodynamic analysis of egg phosphatidylcholine vesicles" *Ann. NY Acad., Sci.* 308, 29-49.

Nam, J.-M., Thaxton, C. S., and Mirkin, C. A. (2003) "Nanoparticle-based bio-bar codes for the ultrasensitive detection of proteins" *Science* 301, 1884-1886.

Monroe, D. (1986) in "Immunoassay Technology" (Pal, S. B., ed.) Walter de Gruyter Co. Berlin, N.Y., pp 167-187.

Niemeyer, C. M., Adler, M., and Blohm, D. (1997) "Fluorometric polymerase chain reaction (PCR) enzyme-linked immunsorbent assay for quantification of immuno-PCR products in microplates" *Analytical Biochem.* 246, 140-145.

Niemeyer, C. M., Adler, M., Pignataro, B., Lanhert, S., Gao, S., Chi, L., Fuchs, H., and Blohm, D. (1999) "Self-assembly of DNA-streptavidin nanostructures and their use as reagents in immuno-PCR" *Nucleic Acids Research* 27, 4553-4561.

New, R. R. C. (1990) "Characterization of Liposomes" in "Liposomes: a Practical Approach" (New, R. R. C., ed.) Oxford University Press, New York, N.Y., pp 105-161.

O'Leary, T. J., Tsai, M., Wright, C., and Cushion, M. T. (1995) "Use of semiquantitative PCR to assess onset and treatment of *Pneumocystis carinii* Infection in rat model" *J Clin. Microbiol.* 33, 718-724.

Payne, N. I., Browning, I, and Hynes, C. A. (1986) "Characterization of proliposomes" *J. Pharm. Sci.* 75, 330-333.

Qin, Q.-P., Lovgren, T., and Pettersson, K. (2001) "Development of highly fluorescent detection reagents for the construction of ultrasensitive immunoassays" *Anal. Chem.* 73, 1521-1529.

Reid, A. H. (1994) "Polymerase chain reaction" in "Advanced Laboratory Methods in Histology and Pathology" (Mikel, U, ed.) *American Registry of Pathology Publications* Washington, D.C., pp 77-110.

Ruzicka, V., Marz, W., Russ, A., and Gross, W. (1993) "Immuno-PCR with a commercially available avidin system" *Science* 260, 698-699.

Sano, T., Smith, C. L., and Cantor, C. R. (1992) "Immuno-PCR: very sensitive antigen detection by means of specific antibody-DNA conjugates" *Science* 258, 120-122.

Sheng, Z.-M., Przygodzki, R. M., and O'Leary, T. J. (2001) "Rapid screening for KIT mutations by capillary electrophoresis" *Clin. Chem.* 47, 1325-1326.

Singh, A. K., Harrison, S. H., and Schoeniger, J. S. (2000) "Gangliosides as receptors for biological toxins: development of sensitive fluoroimmunoassays using ganglioside-bearing liposomes" *Anal. Chem.* 72, 6019-6024.

Smith, I. C. P. and Ekiel, I. H. (1984) in "Phosphorus-31 NMR of phospholipids in membranes" in "Phosphorus-31 NMR Principles and Applications" (Gorenstein, D. G., ed.) Academic Press, New York, N.Y., pp 447-460.

Szoka, Jr., F. and Papahadjopoulos, D. (1978) "Procedure for preparation of liposomes with large internal aqueous space and high capture by reverse-phase evaporation" *Proc. Natl. Acad. Sic USA* 75, 4194-4198.

Szoka, F, and Papahadjopoulos, D. (1980) "Comparative properties and methods of preparation of lipid vesicles (liposomes)" *Ann. Rev. Bioeng.* 9, 467-508.

Tanabe, T., Touma, K., Hamasaki, K., and Ueno, A. (2001) "Fluorescent cyclodextrin immobilized on a cellulose membrane as a chemosensor system for detecting molecules" *Anal. Chem.* 73, 1877-1880.

Wang, J., Chatrathi, M. P., Mulchandani, A., and Chen, W. (2001) "Capillary electrophoresis microchips for separation and detection of organophosphate nerve agents" *Anal. Chem.* 73, 1804-1808.

Wong, W. M., Lam, V. M. S., Cheng, L. Y. L., and Tam, J. W. O. (1988) "Genomic sequence of a Sprague-Dawley rat beta-globin gene" *Nucl. Acids. Res.* 16, 2342.

Wu, H. C., Huang, Y. L., Lai, S. C., Huang, Y. Y., and Shaio, M. F. (2001) "Detection of *Clostridium botulinum* neurotoxin type A using immuno-PCR" *Lett. in Appl. MicroBiol.* 32, 321-325.

Young, K. K. Y., Resnick, R. M., and Myers, T. W. (1993) "Detection of hepatitis C virus RNA by a combined reverse transcription-polymerase chain reaction assay" *J Clin. Microbiol.* 31, 882-886.

In the following description, reference is made to the accompanying drawing, and which is shown by way of illustration to the specific embodiments in which the invention may be practiced. The following illustrated embodiments are described in sufficient detail to enable those skilled in the art to practice the invention. It is to be understood that other embodiments may be utilized and that structural changes based on presently known methodology and/or functional equivalents may be made without departing from the scope of the invention.

Given the following detailed description, it should become apparent to the person having ordinary skill in the art that the invention herein provides a novel immuno-liposome amplification assay and method permitting exploitation of significantly augmented efficiencies while mitigating problems of the prior art.

IV. BRIEF DESCRIPTION OF THE DRAWINGS

FIG. 1 is a representative illustration of an initial step in the practice of the invention.

FIG. 2 is a representative illustration of a subsequent step in the practice of the invention.

FIG. 3 is a representative illustration of a further sequential step in the practice of the invention.

FIG. 4 is a representative illustration of a step following the step illustrated in FIG. 3.

FIG. 5 is a representative illustration of a subsequent step in the practice of the invention.

FIG. 6 is a representative illustration of a rinsing step following the step represented in FIG. 5 in the practice of the invention.

FIG. 7 is a representative illustration of a lysing step following the rinsing step illustrated in FIG. 6.

FIG. 8 represents PCR-type amplification according to the described embodiments of the invention.

FIG. 9 diagramatically represents a gel electrophoresis obtained in accordance with the invention.

Figures 10, 11:
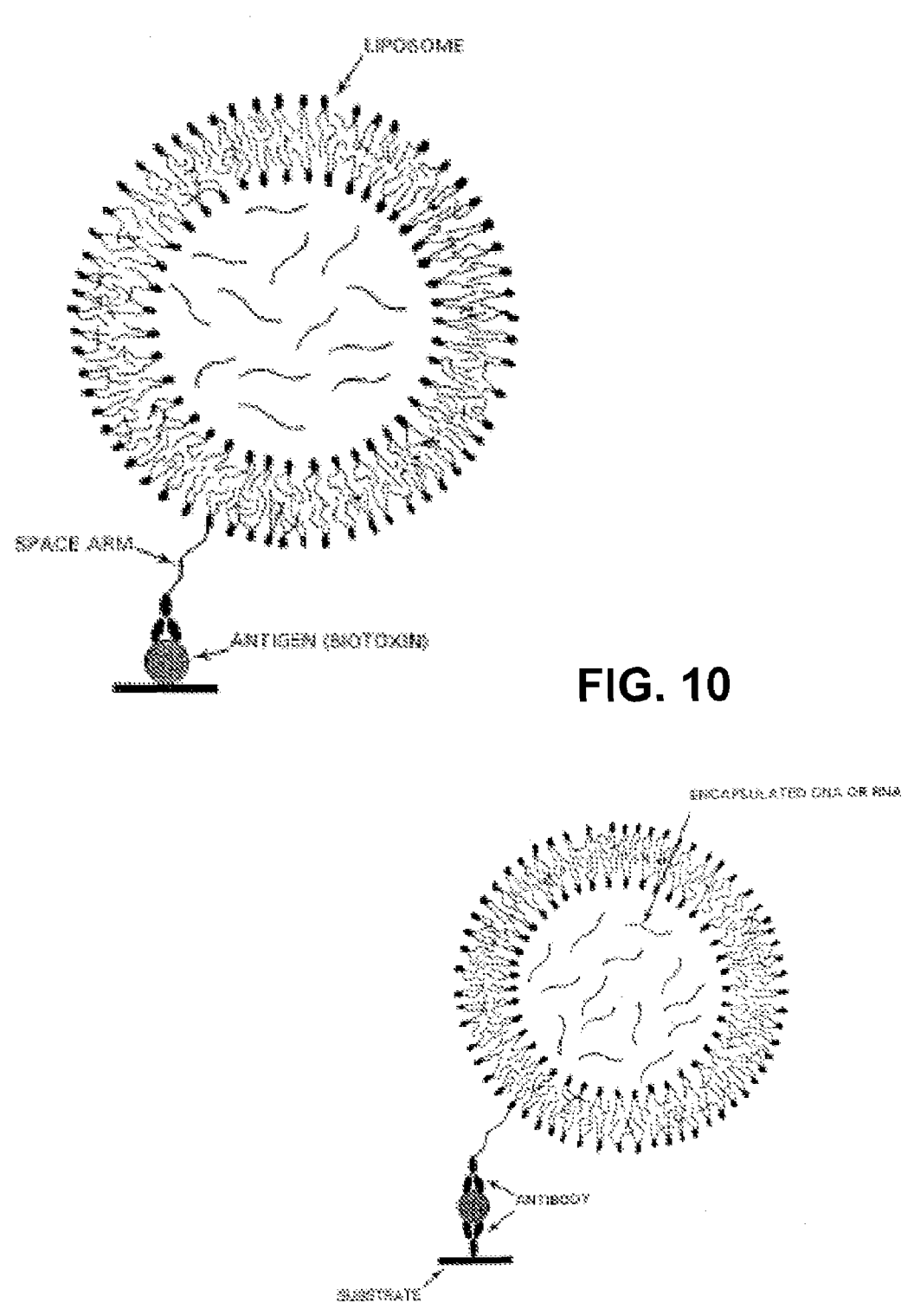

FIG. 10 represents an immunoliposome directly bound to an antigen on a substrate according to the invention.

FIG. 11 represents indirect binding of an antibody complex bound to an immunoliposome and a substrate.

Figure 12:
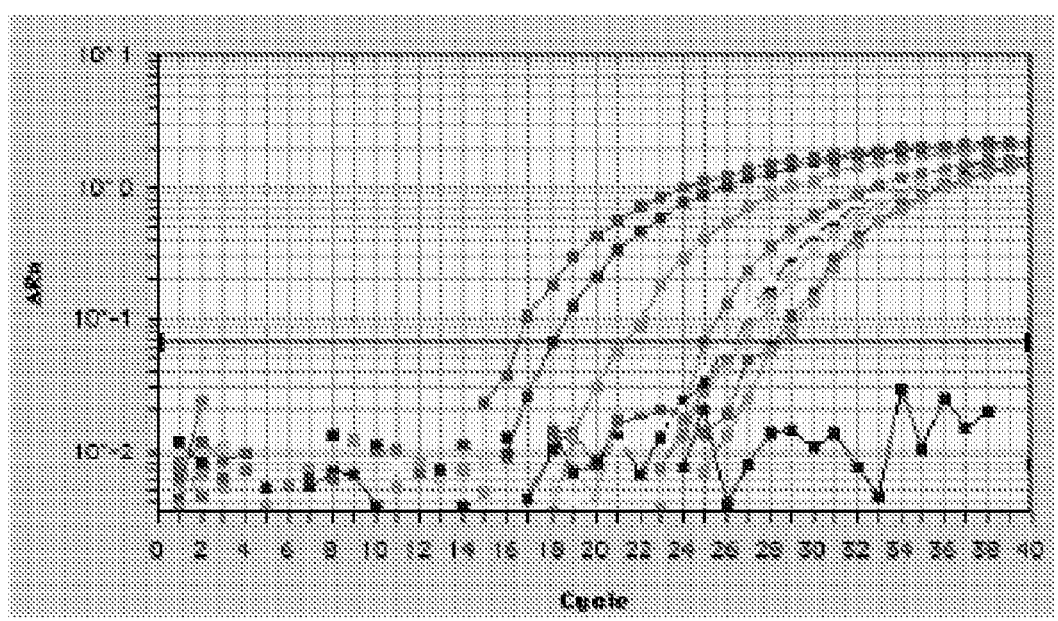

FIG. 12 is a representative plot of the fluorescence response curves for various concentrations of Cholera toxoid B.

Figure 13:
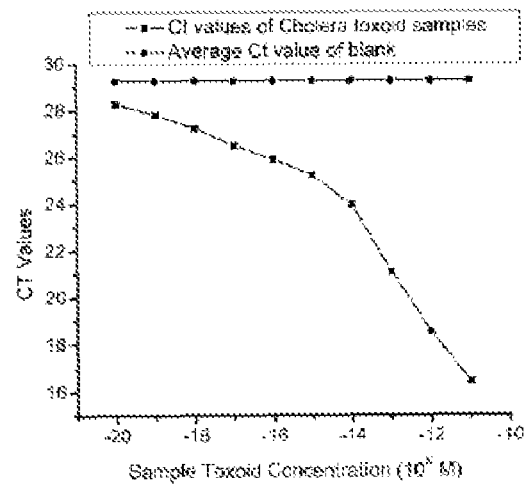

FIG. 13 is a graph representing average Ct values obtained from FIG. 13 plotted against the molar concentration of Cholera toxoid B subunit.

Figure 14:
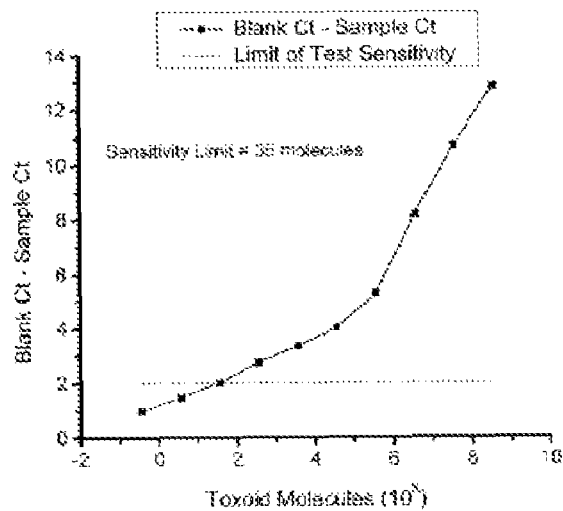

FIG. 14 is shows the points plotted in FIG. 14 re-plotted with changes to each axis of the graph.

V. DETAILED DESCRIPTION OF THE DRAWINGS

This specification is divided into three sections. The first section (A) describes the key elements of the assay with particular emphasis on the variable elements of the assay whose choice depends upon the target compound to be detected and the method to be used to detect the amplified nucleic acid product (such as a PCR product). The second section (B) describes the entire ILNAA assay method in detail by using the detection of cholera toxin as a specific example. The third section provides detailed information on all of the individual steps of the ILNAA assay method with information on alternate approaches for optimizing the assay and quality control procedures.

A. Preparation of DNA Amplification Substrate for Encapsulation

Specific target DNA sequences (one form of amplification substrate) are produced by PCR amplification of a rat *Pneumocystis carinii* gene segment. For assays involving the simultaneous detection of two antigens, target DNA sequences of a rat β-globin gene segment are employed as the second amplification substrate. These sequences have been chosen for experimental convenience only. Virtually any gene target, including plasmids that are not normally found in the samples to be assayed, may be used in the encapsulation process. The primer sequences for *Pneumocystis carinii* have been taken from O'Leary et al. (1995) and those for rat β-globin were based on sequences published by Wong et al. (1988). Primers for amplifying these DNA sequences along with probes useful for their identification are described in Table 1.

TABLE I

Primers and Probes for PCR

| Gene | Primer/Probe | Sequence |
|---|---|---|
| rat β-lobin | primer | 5'GGTGCACCTAACTGATGTTG3' |
| | primer 2 | 5'GCTTGTCACAGTGGAGTTCAC3' |
| | Probe | 5'GATAATGTTGGCGCTGAGGGCCC3' |
| P. carinii | primer 1 | 5'GATGGCTGTTTCCAAGCCCATG3' |
| | primer 2 | 5'GTGACGTTGCAAAGTACTC3' |
| | Probe | 5'ATAAGGTAGATAGTCGAAAG3' |

To prepare amplification substrates, a 0.5 μL sample, taken from a previous PCR reaction in which the amplification substrates have been prepared, is added to a PCR reaction mixture containing 10 mM TrisHCl (pH 8.0), 50 mM KCl, 3 mM $MgCl_2$, 0.5 mM dNTPs, 0.5 µM of each primer (Table 1) and 1 IU Taq polymerase. The sample is overlaid with 25 µL of mineral oil, denatured for 2 min at 94° C., and then subjected to 30 cycles in a thermocycler (Perkin-Elmer 9600 GeneAmp) consisting of a sixty second 94° C. denaturation step, a fifty second 50° C. annealing step, and a fifty second 72° C. elongation step. Following amplification, the amplification substrates are separated from the PCR mixture by gel chromatography and stored in 10 mM Tris-HCl, pH7.4 buffer at a concentration of 1 mg/mL prior to their incorporation into liposomes.

B. Encapsulation of Amplification Substrates into Liposomes

Lipids used in the preparation of liposomes are obtained from Avanti Polar Lipids Inc., Alabaster, Ala. or from Sigma Chemical Company, St. Louis, Mo. All other reagents required for the preparation of liposomes are available from commercial sources and are of the highest grade available. For the preparation of large unilamellar vesicles (LUVs) a Lipex Extruder® (Lipex Biomembranes, Vancouver, Canada) is employed. Nuclepore® filters for use with the Lipex Extruder are obtained from Nuclepore Corp., Pleasanton, Calif.

The lipids to be employed to form the liposomes are weighted out in the desired stoichiometry and mixed by dissolving them in chloroform in a round bottom flask. The solvent is removed under nitrogen, which leaves a thin film of the lipids on the bottom and sides of the flask. Removal of the last traces of solvent is accomplished by desiccating the mixed lipid film under vacuum for 4 hr. The standard lipid mixture used is 1,2-doleoyl-sn-glycero-3-phosphocholine/1,2-dioleoyl-sn-glycero-3-phosphoethamolamine/N-dodecanyl-1,2-dipalmitoyl-sn-glycero-3-phosphoethanolamine (NDPE) (49.9:49.9:0.2 mol). NDPE is the linkage moiety for the antibodies. Other lipid mixtures may be tried when attempting to optimize the assay and minimize the non-specific binding of the immunoliposomes. In some cases phosphatidylethanolamine labeled with the fluorophore lissamine-rhodamine (Texas Red) is incorporated into the bilayers to use in determining the concentration of the liposomes and to visualize the liposomes during the purification steps. The fluorescently labeled phosphatidylethanolamine is obtained from Molecular Probes, Inc. (Eugene, Oreg.).

The gel-purified DNA amplification substrates are then dissolved in 10 mM Tris-HCl, pH7.4 at a concentration of 1 mg/mL.

Resuspending the dried lipid film in aqueous 10 mM Tris-HCl, pH7.4 using a vortex mixer forms multilamellar vesicles (MLVs). The MLVs are allowed to swell in the buffer for 1 hour at 37° C.

The phospholipid MLV dispersion (80 mM total lipid) are converted into small single-shell vesicles (20 nm diameter) by probe tip sonication in an ice bath for 15 min. The sonicated vesicles are freed of large lipid aggregates by centrifugation at 12,000 rpm for 5 min. For amplification substrate encapsulation 20 µmol of sonicated vesicles and 0.1 mg of amplification substrate in 400 µL of Tris-HCl, pH7.4 buffer are combined by vortex mixing with 600 µL of 40% aqueous ethanol containing 5 mM $CaCl_2$. The phospholipid-amplification substrate complexes are dialyzed against 500 volumes of 10 mM Tris-HCl, pH7.4 for 24 hr with two changes of buffer. This method (Bailey and Sullivan, 2000) typically results in a 70% encapsulation efficiency of the amplification substrates inside the closed-shell single-bilayer liposomes.

One alternate method to encapsulate amplification substrates into liposomes is by extruding a suspension of MLVs and amplification substrates through Nuclepore® membranes containing 100 nm pores. The Lipex Extruder® is assembled as described in the manufacturer's literature and two stacked 100 nm Nuclepore® membranes are placed in the filter holder. The MLV suspension (1-10 mL at 1-10 mg/mL total lipid) in buffer containing the amplification substrate (0.1-1 mg/mL) is added to the extruder, which is sealed and pressurized with nitrogen to a level sufficient to produce an extrusion rate of 1-2 mL/min. Depending upon the lipid and amplification substrate concentrations the required pressure can range from 100 to 800 psi.

Once the lipid suspension has been completely extruded the pressure is released and the suspension is reintroduced into the device and the extrusion process is repeated. The lipid suspension is subjected to 25 total extrusion cycles. This process results in the formation of LUVs (with encapsulated amplification substrate) with diameters of 0.08 to 1.1 microns and trapped volumes of 3-7 µL per µmole of lipid (Hope et al., 1985). There are several additional liposome encapsulation procedures (Szoka and Papahadjopoulos, 1980) that could be employed should any difficulties be encountered with the other methods. Principal among these is the reverse-phase evaporation technique of Szoka and Papahadjopoulos (1978), that has proven successful for DNA encapsulation into LUVs.

The amplification substrate-containing liposomes are purified from non-encapsulated amplification substrate by density gradient ultracentrifugation with Ficoll (Fraley et al., 1980). The crude liposomal suspension (0.5 mL) is mixed with 1 mL of 30% (w/v) Ficoll to yield a final Ficoll concentration of 20% (w/v). This suspension is added to a 10 mL, centrifuge tube. Then, 3 mL of 10% (w/v) Ficoll is layered over the liposome solution and 1 mL of normal buffered saline is, in turn, layered over the 10% Ficoll. The tube is spun at 100,000-x g for 30 min at room temperature. The purified amplification substrate containing liposomes are recovered at the interface between the saline and 10% Ficoll layers while the non-encapsulated amplification substrate remains in the 20% Ficoll layer at the bottom of the tube. Ficoll is then removed from the liposomal suspension by dialysis against 3-4 changes of excess isotonic buffer using 100,000 molecular weight cut-off dialysis membranes.

An alternate purification method to remove non-encapsulated amplification substrates from the liposomal suspension is gel chromatography using Sephadex G-50 or Sepharose 4B (Fry et al., 1978; Huang, C., 1969). This technique has the advantage of not requiring dialysis to remove Ficoll, but the liposomes are diluted as they elute from the column and will typically need to be concentrated with an Amicon concentrator using PM-10 membranes. If DNA or RNA is found to adhere to the outer surface of the liposomes it can be removed by digestion with DNase or RNase as described by Loyter et al. (1983). The enzyme will not cross the bilayer and degrade the encapsulated DNA or RNA. The liposomal preparation can then be re-purified by Ficoll density gradient centrifugation or gel chromatography.

In order to ensure vesicle integrity and to prevent vesicle leakage it is important to replace the original extravesicular amplification substrate solution with an isotonic buffer after purification. The suitability of the buffer can be checked by diluting the liposomes in the presumed isotonic buffer and monitoring the turbidity at 400 nm for 1-2 minutes. If a change in turbidity is detected (due to swelling or shrinking of the vesicles) the buffer composition can be changed accordingly.

C. Covalent Attachment of Antibodies to Liposomes

Derivatized phospholipids for attaching antibodies to liposomes are available from Avanti Polar Lipids Inc. EDCl (1-ethyl-3-(dimethyl aminopropyl)-carbodiimide) and all other reagents are obtained from Sigma Chemical Company.

Phosphatidylethanolamine (PE) can be derivatized with dicarboxylic acids such that the PE moiety bears a free carboxylic group. After incorporation into liposomes this free carboxyl group can be activated so as to covalently bind to amino groups on proteins, including antibodies. By using dicarboxylic acids with different numbers of carbons, the length of the "spacer arm" between the antibody and the bilayer can be varied. A length of 6-12 carbons has been shown to be optimal for the efficiency of antibody binding and the minimization of non-specific binding of proteins to the liposomal surface (Kung and Redemann, 1986). We use N-dodecanyl-1,2-dipalmitoyl-sn-glycero-3-phosphoethanolamine (NDPE) as the covalent attachment site for antibodies on the liposomal surface.

NDPE is incorporated at a level of 0.2 mole % in the lipid film used to form the liposomes as was described above. The carboxylic group (0.05 μmol/mL) is activated by incubation for 1 hour with EDCl (2.5 mg/mL) in phosphate buffered saline at pH 5.0. The antibody (0.05 mg/mL) is then added and the ionic strength of the solution is increased by adding 50 μL/mL of 1M NaCl and adjusting the pH to 8.0. The reaction mixture is allowed to incubate overnight at 4° C. This procedure has been optimized to yield an average of one antibody bound per liposome, which is what is desired for the purpose of our assay. However, this reduces the yield based upon antibody to about 60 mol % (Kung and Redemann, 1986).

Unbound antibodies and EDCl are separated from the amplification substrate-containing immunoliposomes using the same Ficoll density centrifugation procedure used to separate unencapsulated amplification substrates from immunoliposomes. The immunoliposomes are recovered from the interface between the saline and 10% Ficoll layers and the unattached antibodies and EDCl are recovered from the bottom 20% Ficoll layer. Alternately, the unreacted antibodies can be removed by gel chromatography on Sephadex G-50 or Sepharose 4B.

Although the above procedure has proven successful for the covalent attachment of antibodies to liposomes alternate procedures cab be tried if the carboxylic acid linkage is observed to reduce the antigen binding activity or specificity of the antibodies. Antibody Fab' fragments can be bound to liposomes via PE activated with N-succinimidyl pyridyl propionate (SPDP) by way of the free thiol group on the Fab' fragment (Martin et al., 1990). This linkage method would prove useful if normal bivalent antibodies prove unacceptable for a given assay. Antibodies can also be covalently coupled to liposomes containing monoglycolipids via a Schiff base. The bilayer-bound glycolipid sugar moieties are oxidized with periodate to form aldehydes, which then react with primary or secondary amino groups on the antibody. Any unreacted aldehydes are then reduced with cyanoborohydride (Heath et al., 1981).

D. Characterization and Storage of Immunoliposomes

Fluorescent reagents are purchased from Molecular Probes Inc. All other reagents are purchased from Sigma Chemical Co. Fluorescence measurements are made with a Jasco model FP-777 fluorescence spectrofluorimeter (Jasco Inc., Easton, Md.). Liposomal size is determined with a Nicomp model 370 laser light scattering autocorrelation spectrometer equipped with a 50 mW 488 nm Argon laser (Particle Sizing Systems, Palo Alto, Calif.). Phosphrous-31 NMR measurements of lipid morphology and bilayer permeability are performed with a Bruker 400 MHz wide-bore NMR spectrometer equipped with a 10 mm broad-band observe probe tuned for phosphorus with broad-band proton decoupling (Bruker Biospin Inc., Billerica, Mass.).

Lipid concentration can be determined through fluorometric assay by adding 0.05 mol % PE labeled with the fluorophore Texas Red (excitation max: 589 nm, emission max: 615 nm) to the lipid films used to prepare the liposomes. Prior to fluorometric measurement the liposomes are solubilized to form a micellar solution by the addition of 100 μL of 5% (w/v) Triton X-100 per 2 mL of liposome solution with heating at 37° C. for 10 min with occasional vortexing. Alternately, lipid concentration can be determined through the measurement of the phospholipid concentration by the method of inorganic phosphate (Gomori, 1942). Either of these measurements, coupled with the known composition of the original lipid film, will yield the total lipid concentration of the liposomal solution.

DNA concentration is determined through fluorometric assay using the Molecular Probes "PicoGreen®" nucleic acid (dsDNA) assay kit (excitation max: 480 nm, emission max: 520 nm). RNA concentration is determined through fluorometric assay using the Molecular Probes "RiboGreen®" RNA assay kit (excitation max: 480 nm, emission max: 520 nm). These absorption and emission maxima are sufficiently displaced from those of Texas Red that the phospholipid probe will not interfere with the DNA or RNA measurements. Prior to fluorometric measurement the liposomes are solubilized to form a micellar solution by the addition of 100 μL of 5% (w/v) Triton X-100 per 2 mL of liposome solution with heating at 37° C. for 10 min with occasional vortexing. This will release the encapsulated DNA or RNA as the liposomes convert to micelles. Determination of the DNA or RNA concentration immediately following the encapsulation step will yield the total nucleic acid present (encapsulated+non-encapsulated=total nucleic acid). Determination of the DNA or RNA concentration following purification after liposome formation or antibody binding steps (where non-encapsulated nucleic acid has been removed) will yield the concentration of encapsulated nucleic acid. The ratio of these two measurements yields the encapsulation efficiency. The number of amplification substrate molecules encapsulated per liposome is calculated as described below.

Protein (antibody) concentration is determined by fluorometric assay (Bridges et al., 1986) with fluorescamine (excitation max: 383 nm, emission max: 478 nm). The absorption and emission maxima are sufficiently displaced from those of Texas Red that the phospholipid probe will not interfere with the protein measurements. Prior to fluorometric measurement the liposomes are solubilized to form a micellar solution by the addition of 100 μL of 5% (w/v) Triton X-100 per 2 mL of liposome solution with heating at 37° C. for 10 min with occasional vortexing. The number of antibody molecules bound per liposome is calculated as described below.

The hydrated outer diameter of the immunoliposomes is determined by laser light scattering with a Nicomp autocorrelation spectrometer equipped with a 50 mW 488 nm Argon laser (Payne et al., 1986). The liposomal diameter, along with the average headgroup area of the lipids at the bilayer surface (~71 $Å^2$ for PC and 19 $Å^2$ for cholesterol) and an estimate of the bilayer thickness (~36 Å), will yield the number of lipid molecules per liposome. These calculations are described in detail in Mason and Huang (1978). The total number of lipid molecules per liposome and the total lipid concentration yields the concentration of liposomes in the solution. This value, along with the antibody and encapsulated amplification substrate concentrations, yield the number of bound antibody molecules per liposome and the number of encapsulated amplification substrate molecules per liposome.

Phosphorous NMR will be used to confirm that the immunoliposomes form a single-bilayer closed-shell morphology and that no non-lamellar aggregates are present in the preparations. This is accomplished by examination of the line shape of the phosphorus spectrum of the phospholipid headgroups. The presence of non-lamellar structures, such as micelle or hexagonal phases, effect the phosphorus spectrum in well-defined ways and will be easily detected (Smith and Ekiek, 1984). Phosphorus NMR will also be used to ensure that the liposomes contain, on average, only a single bilayer and that the bilayers are not leaky. A bilayer-impermeable chemical shift reagent, such as praseodymium (III) chloride, is added to the liposome solution, which will alter the chemical shift of the phosphorus signal originating from the phospholipids in the outer half of the liposomal bilayer. A 1:1 ratio of the signals originating from the inner and outer (shifted) bilayer halves indicate that the liposomes possess, on average, a single bilayer. The stability of this ratio over time indicates that the liposomes are intact and not leaky since the shift reagent has not been able to diffuse to the inside of the liposomes. Any problems with the morphology or bilayer permeability of the immunoliposomes revealed by our phosphorus NMR measurements are corrected by altering the conditions by which the liposomes are produced or stored.

The optimal storage conditions are established for each immunoliposome formulation. These will include room temperature versus cold storage, storage as dilute versus concentrated solutions and other variations. Physical measurements are repeated over time as described above to determine the effect of storage on the integrity of the liposomes, the rate of leakage of the encapsulated amplification substrate, the aggregation state of the liposomes, and the activity of the covalently bound antibodies. These studies lead to a determination of the optimal storage conditions for the immunoliposomes and an estimate of their shelf life.

E. Immunoassay Methods

This section describes illustrative immunoassay methods that are be used in conjunction with the immunoliposomes. Variations of this basic method that can be explored in order to optimize the performance of the assay and minimize the non-specific binding of the immunoliposomes will also be described. The PCR methods and the techniques to be used to visualize and quantitate the amplification substrate are described below.

Microtiter plates (96-well and strip) are obtained from Fisher Scientific (Pittsburgh, Pa.). Antibodies are obtained from US Biologies, Boehringer Manheim Corp., Sigma Chemical Company, Accurate Chemical and Scientific Corp., Westbury, N.Y., and other vendors or laboratories. Fluorescent phospholipid probes are obtained form Molecular Probes, Inc. Other immunoassay reagents and proteins are obtained from Sigma Chemical Co. Fluorescence measurements are made with a Jasco model FP-777 fluorescence spectrofluorimeter. The microtiter plate washer used in the immunoassays is a Biomek 2000 from Beckman Instruments, Inc. (Palo Alto, Calif.).

The basic immunoassay method to be employed is a variation on published techniques (Singh et al., 2000; Crowther, 1995) that have been shown to work for immunoassays using fluorescently labeled liposomes. This method consists of the following steps which are illustrated schematically in FIGS. 1-9:

1. Antibodies directed against the antigen of interest are dissolved at a concentration of 10 µg/mL in phosphate buffered saline (PBS) at PH 7.4. A volume of 125 µL of the antibody solution is added to each well of a microtiter plate, which is then sealed and incubated overnight at 4° C. on a shaker bath. This process will result in the immobilization of the antibodies on the sides and bottom of the wells. (See FIG. 1). The wells of the microtiter plate are then aspirated and washed 2× with PBS using a plate washer.

2. As represented in FIG. 2, the wells are blocked by adding 250 µL of a BSA solution (10 mg/mL) to each well followed by incubation at 4° C. for 4 hours. The plates are then aspirated and washed 3× with PBS.

3. Various dilutions of antigen are added to the wells of the microtiter plate, as depicted in FIG. 3, along with PBS (control solution). The plate is incubated at 37° C. for 1 hour and then aspirated and washed 5× with PBS. This process results in the binding of the antigen to the corresponding immobilized antibodies in the wells of the microtiter plate. (See FIG. 4).

4. FIG. 5 is representative of the next step, comprising adding a 200 µL aliquot of the appropriate immunoliposome solution (25 µmolar in total lipid) is added to each well of the microtiter plate and the immunoliposomal solution is incubated at 37° C. for 1 hour. The wells are then aspirated and washed 5× with PBS to remove free and non-specifically bound immunoliposomes and finally filled with 300 µL, of PBS.

5. To remove any contaminating DNA or amplification substrates outside of the immunoliposomes 10 µL of DNase 1 (82 IU/µL) is added to each well. The plate is then sealed and incubated at 37° C. for 30 min followed by heat inactivation of the DNase I by heating the microtiter plate to 80° C. for 10 min as represented by FIG. 6.

6. FIG. 7 illustrates lysing of the immunoliposomes with the addition of 15 µL of 5% (w/v) Triton X-100. The plate is then sealed and incubated at 37° C. for 10 min on a shaker bath. This process lyses the immunoliposomes and releases the amplification substrates into the bulk solution. A 0.5 µL aliquot is extracted from each well and the released amplification substrates are amplified by PCR.

F. Optimization of the Immunoassay

The following describes steps to be taken to optimize the immunoassay conditions in order to maximize selectivity and sensitivity, and to minimize the non-specific binding of immunoliposomes to the microtiter plate wells as well as variations on the type of immunoassay that can be performed, the specific immunoassay conditions, the characteristics of the immunoliposomes, and the liposomal lysis conditions.

This discussion describes two ways to immobilize the antigen to the microtiter plate wells. One technique is to immobilize the antigen directly and then add the antigen-specific antibody detection system. This approach is illustrated in FIG. 10 and has been shown to be capable of detecting apolipoprotein E at concentrations as low as 10 femtograms/mL (Ruzicka et al., 1993).

The second method, illustrated in FIG. 11, is the indirect antigen binding method. In this method an antigen-specific antibody is first immobilized in the wells and is subsequently used to capture the antigen upon addition of a sample solution containing free antigen. The latter method is generally believed to lead to higher sensitivity, however, both approaches can be tried. In addition, antibody competition forms of the assay can be tried to see if this approach leads to superior sensitivity. Other variations on the type of immunoassay employed can be tried as deemed necessary (Crowther, 1995).

Once an optimal type of immunoassay has been selected as describe above, the specific conditions to be employed during this assay procedure are varied in order to optimize sensitivity and selectivity and minimize non-specific binding of the immunoliposomes. These conditions are:

1) The type of microtiter plate used;
2) The type of blocking protein used along with its concentration and incubation time;
3) The type of washing buffers used and the number of wash cycles performed for the various assay steps;
4) The incubation time and temperature employed for both the antigen and immunoliposomes binding steps; and
5) The concentration of all reagents used in the various steps.

The types of microtiter plates that can be tried include Fisher V-96 polypropylene, Nuc® MaxiSorb, Falcon® Pro-Bind polystyrene, Costar® polystyrene, and Immulon® High-Binding. Types of blocking buffers that can be tried include BSA, fetal calf serum, normal rabbit and horse serums, casein, gelatin, dextran sulfate, and nonfat dried milk. Detergents cannot be used as they would disrupt the liposomes. All blocking buffers that are tried must be tested for their ability to disrupt the liposomes. Other variations of the immunoassay conditions may be attempted as deemed necessary (Crowther, 1995).

Varying the properties of the immunoliposomes can be tried, principally to minimize nonspecific binding of the liposomes to the wells of the microtiter plates and the blocking agent. The properties that can be varied include:

1) The size of the liposomes;
2) The fluidity of the bilayer;
3) The length of the spacer arm used to attach the antibody to the bilayer surface;
4) The overall charge of the liposomes;
5) The charge density of the liposomes; and
6) The polarity of the extravesicular liposomal surface.

The size of the liposomes can be varied over a range of 80 to 250 nm without significantly altering their ability to encapasulate amplification substrate (Hope et al., 1985). This is accomplished by employing Nuclepore® membranes of the corresponding size during the extrusion process used to form the LUVs. Bilayer fluidity can be decreased by adding or increasing the mol % of cholesterol in the bilayer or by using phospholipids with saturated fatty acid chains. Conversely, bilayer fluidity can be increased by deleting or decreasing the mol % of cholesterol in the bilayer. The length of the spacer arm used to attach the antibody to the bilayer surface can be varied from 6 to 12 without significantly altering the efficiency of the linkage reaction (Kung and Redemann, 1986). The net charge and charge density of the bilayer can be altered by changing the lipid composition of the bilayer. A net negative charge can be introduced into the bilayer by the inclusion of phosphatidylglycerol or phosphatidylserine and a net positive charge can be introduced by the inclusion of stearylamine. The polarity of the bilayer can be increased without the introduction of a net charge by adding glycolipids to the bilayer.

If DNA or RNA contamination of the assay solutions from background nucleic acid or from amplification substrates that have leaked from the immunoliposomes proves to be a problem the DNA or RNA will be degraded by treatment with DNase or RNase as described by Loyter et al. (1983). To remove any contaminating nucleic acids or amplification substrates outside of the immunoliposomes 10 µL of DNase or RNase (82 IU/µL) is added to each well. The plate is then sealed and incubated at 37° C. for 30 min followed by heat inactivation of the DNase or RNase by heating the microtiter plate to 80° C. for 10 min.

The next step involves lysis of the Immunoliposomes. Triton X-100 may be used to lyse immunoliposomes and release the encapsulated amplification substrates for PCR amplification. This is accomplished by the addition of 100 µL of 5% (w/v) Triton X-100 per 2 ml of liposome solution and heating briefly at 37° C. for 10 min with occasional vortexing. If detergent lysis is found to be incompatible with some aspect of the assay additional solubilization methods can be tried. These would include liposomal lysis with alcohols, such as ethanol, (New, 1990) or lysis with low concentrations of melittin as described by Monroe (1986).

F. PCR Amplification and Detection of Amplification Substrates

This section describes the methods to be used to perform the PCR amplification of the amplification substrates released after liposomal lysis of the immunoliposomes and their subsequent detection by gel electrophoresis, capillary electrophoresis and the Taqman® assay.

Taq polymerase is obtained from Perkin-Elmer (Foster City, Calif.) and all other PCR and gel electrophoresis reagents are obtained from Pharmacia Biotech (Piscataway, N.J.). The DNA template and primers are available in our laboratory or are obtained from commercial sources. PCR is performed on a Perkin-Elmer model 9600 GencAmp programmable thermocycler. Gel electrophoresis is performed with a submarine gel rig and power supply from Pharmacia Biotech. Capillary electrophoresis is performed with a Perkin-Elmer ABI model 310 genetic analyzer (Foster City, Calif.).

FIG. 8 represents amplification following lysis of the immunoliposomes. For this illustrative step, a 0.5 µL aliquot is extracted from each microtiter plate well and subjected to PCR amplification. Each 0.5 µL sample is added to a PCR reaction mixture containing 10 mM Tris-HCl (pH 8.0), 50 mM KCl, 3 mM $MgCl_2$, 0.5 mM dNTPs, 0.5 µM of the appropriate primers (see Table 1) and 1 IU Taq polymerase. The sample is overlaid with 25 µL of mineral oil, denatured for 2 min at 94° C., and then subjected to 30 (or more) cycles in a thermocycler (Perkin-Elmer 9600 GeneAmp) consisting of a sixty second 94° C. denaturation step, a fifty second 50° C. annealing step, and a fifty second 72° C. elongation step. The amplified PCR product is ready for gel or capillary electrophoresis.

Agarose gel electrophoresis of the amplified nucleic acid product is conducted according to established procedures (Reid, 1994), schematically depicted in FIG. 9. Briefly, 2 g of low-melt and 0.5 g of medium-melt agarose are combined with TBE buffer (0.89 M Tris, 0.89 M boric acid, 2 mM EDTA, pH8.0) and melted by heating in a microwave oven, The mixture is cooled to 50° C., ethidium bromide is added, and the mixture is poured into a gel mold. After the gel slab has solidified it is added to the gel apparatus and covered with TBE buffer. The PCR products and appropriate MW standards are combined with loading buffer and injected into the wells of the gel, which is then electrophoresed for 1.5 to 2 hours. When the electrophoresis is complete the gel is viewed with a transilluminator to visualize the DNA bands. The gel can be photographed for documentation purposes. The intensity of the PCR product band that appears on the agarose gel will provide only a semi-quantitative measure of the amount of antigen present in the original sample. Thus, agarose gel electrophoresis is intended more as a qualitative "present or absent" detection method.

A more quantitative measure of the PCR-amplified product, and thus of the antigen present in the original sample, can be obtained with a fluorescent-based capillary electrophoresis assay (Sheng et al., 2001). For this assay, the PCR reaction is carried out as describe above. Following PCR amplification a 1:10 dilution of the PCR reaction is labeled with a fluorescent probe by incubation with 0.5 µL of TAMRA-labeled standard and 12 µL of formamide for 5 min at 95° C. This mixture is then loaded into a Perkin-Elmer ABI 310 genetic analyzer for analysis of the PCR fragments. The result of this analysis is a chromatogram with one unique peak for each of the different amplification substrate nucleotide length fragments in the mixture. The area under these peaks is proportional to the amount of the amplification substrate in the mixture and, with calibration, yields the amount of antigen present in the original sample.

Real-time PCR quantitation of PCR-amplified amplification substrates is determined with an ABI PRISM model 7700 Sequence Detector (PE Applied Biosystems, Foster City, Calif.) using their Taqman® assay. Briefly, an appropriate fluorescent-labeled probe for the amplification substrate being used is chosen using the "Primer Express" software of the instrument and this TAMRA-labeled probe is generated in the laboratory or ordered from PE Applied Biosystems.

A 0.5 µL aliquot from each microtiter plate well is transferred to a fresh microtiter plate and the appropriate PCR reagents and labeled probe are added. The generation of amplified product is monitored by fluorescence emission during the PCR cycles (up to 30) and the threshold cycle (Ct) of each well is determined as the cycle number at which the fluorescent signal exceeds that of the blank. Thus, the lower the Ct value the higher the initial concentration of amplification substrate in that well. A standard curve is generated by performing the assay using serial dilutions of a know concentration of antigen.

DETAILED EXAMPLE

The following recites a specific example of using the invention in connection with the detection of Cholera toxin using real-time PCR for quantifying the amount of toxin present. In this case, a monosialoganglioside ($GM_1$) a ganglioside specific for Cholera toxin, was used as the specific receptor. The immunoliposomes were formed to encapsulate an amplification substrate, which in this case, comprised 50 copies of an 85 base-pair gene fragment for human $\beta_2$-microglobin. This gene fragment (amplicon) serves as the detection agent to quantify the amount of Cholera toxin present in the test sample when amplified by real-time PCR. Notably, the human $B_2$-microglobin gene fragment is chosen strictly for convenience. Any other amplicon can be used and incorporated into the immunoliposomes using this method.

Formation of Immunoliposomes

1) To a volume of 2 mL of chloroform is added 40 mg of 1,2-dioleoyl-sn-glycero-3-phosphocholine (DOPC), 4 mg of lissamine-rhodamine-1,2-dihexadecanoyl-sn-glycero-3-phosphoethanolamine (rhodamine-DHPC), and 2 mg of monosialoganglioside (GM1). The mole ratio of the three components in this solution is 92.2:5.43:2.36. The rhodamine-DHPC is a fluorescent phospholipid that is incorporated into the liposomes to serve as a visualization aid during the formation and purification of the immunoliposomes. It does not interfere with real-time PCR detection of the gene products using the Taqman assay described below.

2) The solution is added to a test tube and the chloroform is removed by incubation in a water bath (heated to 45° C.) under a stream of nitrogen gas. Residual solvent is then removed under high vacuum for 4 hr.

3) The dried lipids are dispersed in 10 mM Tris buffer, pH 7.4, at a concentration of 80 mM total lipids. Small unilamellar vesicles (SUVs) are formed by sonication with a probe-tip sonicator. A sonication program (10 cycles of 4-min on, 1-min off) is used and the test tube containing the lipid mixture is immersed in an ice bath throughout the process to minimize sample heating.

4) The resulting SUVs are centrifuged at 12,000 rpm in a micro-centrifuge for 5 min to remove non-dispersed lipid and titanium from the probe tip. The size of the liposomes are determined by dynamic light scattering using any suitable instrument that can measure particle sizes from 10-1,000 nanometers diameter. The diameter of the SUVs should be 35-40 nanometers.

5) Immunoliposomes are formed by mixing SUVs (250 μl, 20 μmol total lipid) and amplicon (100 μg) with Tris buffer, pH7.4, to give a total volume of 400 μl. To this mixture is added 600 μl of ethanol-calcium chloride solution (5 mM calcium chloride in 10 mM Tris, pH7.4, containing 47.5% (v/v) ethanol). The solution is added drop-wise over approximately 30 seconds with maximum vortex mixing. The resulting lipid complex is dialyzed against 500 volumes of phosphate-buffered normal saline, pH7.4, (PBS) for 24 hr with two changes of buffer.

6) The size of the resulting immunoliposomes are determined by dynamic light scattering as described above for the SUVs. The diameter of the immunoliposomes should be 100-180 nanometers.

Purification of the Immunoliposomes

1) The liposome suspension (0.2 ml) is mixed with 0.4 ml of 30% (w/v) Ficoll dissolved in PBS to give a final concentration of 20% Ficoll. The liposome suspension is transferred to an ultracentrifuge tube in a swinging-bucket rotor.

2) A layer (1.2 ml) of 10% (w/v) Ficoll in PBS is gently layered on top of the liposome suspension. This upper Ficoll layer is covered with a 0.4-mL layer of PBS.

3) The preparation is centrifuged for 30 min at 100,000×g at room temperature. The liposomes are collect at the interface between the saline and 10% Ficoll layers. Unentrapped DNA remains in the lowest Ficoll layer.

4) The purified immunoliposomes are dialyzed against 500 volumes of PBS follow by 500 volumes of 10 mM Tris buffer, pH7.4. The immunoliposomes are then stored in a refrigerator at 4° C. until needed. We have determined that immunoliposomes can be stored in this manner for up to 6 months without any degradation of the lipid bilayer or loss of entrapped amplicon.

5) The above procedure was adapted from Bailey, A. L. and Sullivan, S. M. (2000) "Efficient encapsulation of DNA and plasmids in small neutral liposomes induced by ethanol and calcium" *Biochemica et Biophysica Acta* 1468: 239-252.

Immunoliposome ELISA Assay Method

1) The inner 60 wells of a 96-well Corning flat microtiter plate (Corning EIA high binding, Cat#9018, Corning, Inc., Science Products Division, Corning, N.Y.) are coated with monoclonal antibody (anti-cholera toxin B subunit). Each well receives 150 μl of diluted antibody (1.0 μg/ml) in coating solution or coating solution only (blank). The coating solution is obtained from Kirkegaard & Perry Labs (KPL), Gaithersburg, Md. (Cat#50-84-00). The microtiter plate is covered with a plate sealer, and the plate is incubated at 4° C. on a plate shaker at 600 rpm for 18 h.

2) The coating solution is aspirated, and the wells are washed 5 times with 2 mM imidazole, 0.02% (w/v) Tween-20 in PBS (PBST, KPL, Cat#50-63-00) using a microplate washer. The wells are then blocked with 300 µl/well of 1% (w/v) BSA in PBS (KPL, Cat#50-61-00, 1:10 dilution) for 2 h at room temperature.

3) The blocking solution is aspirated, and the wells are washed with PBST twice and then exposed to 150 µl dilutions of cholera toxin B fragment or buffer (blank) at room temperature for 1 hour. The toxin solution is aspirated, and the wells are washed 5 times with PBST, followed by washing 2 times with PBS.

4) A volume of 150 µl of liposome blocking solution (2.0 µmol/ml, 1:1000) is dispensed into the plate wells, and the microtiter plate is incubated at room temperature for 1 hr. These "blocking" liposomes serve to reduce non-specific binding of the immunoliposomes to the microtiter plate wells. The blocking liposomes are prepared exactly as described above, except that no ganglioside or amplicon is added during the preparation.

5) The liposome blocking solution is aspirated, and the wells are washed 3 times with PBS. A volume of 150 µl of the immunoliposome solution (0.8 µmol/ml, 1:1000) is then dispensed into the wells, and the microtiter plate is incubated again at room temperature for 1 hour.

6) The liposome solution is aspirated, and the wells were washed 10 times with PBS. A volume of 100 µl/well of lysis buffer (10 mM Triton X-100, 10 mM borate buffer, pH 9.0) is added to the wells, and the plate is shaken on a plate shaker for 15 min at 600 rpm. The lysis buffer serves to rupture the membranes of the immunoliposomes releasing the encapsulated amplicons.

Real-Time Quantitative PCR

1) Real-time PCR quantitation is performed with an ABI PRISM model 7700 sequencer (PE Applied Biosystems, Foster City, Calif.) using their Taqman assay. This assay employs a fluorescent probe that binds to a 17 base segment of the human $\beta_2$-microglobin amplicon. A fluorescent chromophore (FAM) attached to one end of this probe is quenched by a second chromophore (TAMRA) that is attached to the opposite end of the probe. As the amplicon is replicated during PCR this probe is degraded, resulting in the release of the FAM into solution where it yields a fluorescent signal. The PCR cycle number where the concentration of FAM is high enough to yield a detectable signal above the background level is referred to as the threshold cycle number (Ct).

2) The sequences of the primers and the fluorescent-labeled probe for the $\beta_2$-microglobin amplicon were selected using the Primer Express software of the ABI PRISM model 7770. The two primers used are:

```
5'-TGA CTT TGT GAC AGC CCA AGA TA-3';
and

5'-AAT CAA AAT GCG GCA TCT TC-3'
```

The fluorescent probe used is:

```
5'-[FAM]-TGA TGC TGC TTA CAT GTC TCG ATC
CCA-[TAMRA]-3'
```

3) Serial dilutions of known concentrations of amplicon were used to generate a standard curve. The concentration of the amplicons was determined spectrophotometrically.

4) A 2.0 µL aliquot from each microtiter plate well is added to a PCR reaction mixture containing 10 mM Tris-HCl (pH 8.0), 50 mM KCl, 3 mM MgCl$_2$, 0.5 mM dNTPs, 0.5 µM of each primer, 10 µM of the fluorescent probe, and 1 IU of AmpliTaq Gold (PE Applied Biosystems). The sample is overlaid with mineral oil, denatured for 2 min at 94° C., and then subjected to 40 cycles in the ABI PRISM 7700 each consisting of a sixty second denaturation step at 94° C., a fifty second annealing step at 50° C., and a fifty second elongation step at 72° C.

Results

1) A representative plot of the fluorescence response curves for various concentrations of Cholera toxoid B subunit is shown in the graph of FIG. 12. The curve on the extreme right was obtained with a sample blank containing no toxoid. All of the curves exhibit an initial phase where the fluorescent signal does not increase above the background with increasing cycles of PCR. The initial phase is followed by an abrupt increase in fluorescence intensity followed by a slow parabolic increase in intensity. Finally, the curves reach a plateau value as the amount of intact probe is depleted. The initial abrupt increase in the fluorescent intensity above the background is defined as the threshold cycle value (Ct). The Ct value is directly proportional to the initial concentration of amplicon in the corresponding ELISA plate well from which the sample was taken. This amplicon concentration, in turn, is directly proportional to the amount of Cholera toxoid present in the plate well. The fluorescence plots and the Ct values are produced automatically by the ABI PRISM model 7700 software.

The graph of FIG. 13 is a plot of the average Ct values, taken from five real-time PCR assays like that shown above, versus the molar concentration of Cholera toxoid B subunit used for the ELISA assays. The upper dotted line is the average Ct value obtained with the sample blanks. The standard deviations of the average sample and blank Ct values were all less than 0.05×Ct (less than 5% error). This level of accuracy was realized for multiple samples within the same ELISA plate or for multiple samples prepared in different ELISA plates.

FIG. 14 represents the data from FIG. 13 re-plotted in the figure below, but with changes to each axis of the graph. Each ELISA well contains 150 µL of toxoid subunit prepared from samples with the molar concentrations indicated in the above figure. Thus, the number of toxoid molecules in each well is given by the expression: $(150 \times 10^{-6}) \times M \times N$, where M is the molar concentration of toxoid and N is Avogadro's number. Accordingly, in FIG. 14 the x-axis is now the number of molecules detected per ELISA plate well. The sensitivity of the ILNAA is a function of the difference between the Ct value observed for the sample blank (no toxoid) and the Ct value observed for a given sample. Accordingly, in the plot below, the y-axis in now the Ct value of the blank minus the Ct value of the toxoid samples (Blank Ct–Sample Ct). Sample Ct values are taken to be reliable when they exceed the blank Ct by a value greater than 2. Thus, the sensitivity limit is shown on the graph as a dotted line located at Blank Ct−Sample Ct=2. Given this criterion, the sensitivity limit for the Cholera toxoid ILNAA is 35 toxoid molecules.

Further Assay Approaches

1. The below described approach describes a further embodiment of the inventive method of this invention where magnetic micro-particles (magnetic beads) are used as the immobile phase instead of microtiter plates. In this method, multiple copies of specific receptor molecules are attached by covalent or non-covalent means to the surface of magnetic beads. By a specific receptor molecule, we refer to a molecule that serves to unambiguously identify a target compound (or a class of target compounds) by tightly and specifically binding to (or reacting with) that compound and no other. The magnetic bead—receptor molecule conjugate is added to a test sample (such as an environmental water sample or a biological fluid sample) and allowed to bind the target compound that is present in the test sample. The magnetic bead complex is then isolated by magnetic precipitation and resuspended in fresh buffer in a fashion analogous to the gold particle method described by Nam et al., *Science* 301, 1884 (2003). The amount of the target compound that has been bound by the magnetic bead-receptor molecule conjugate is then assayed using the ILNAA method as described in this addendum and in the patent application.

Another embodiment of the method contemplates the entire ILNAA being performed with a micro-fabricated device (lab-on-a-chip). This device would consist of a micro-chamber where specific receptors for the target compound have been immobilized. Micro-flow channels leading into and out of this micro-chamber would allow a test solution to flow through the micro-chamber where the specific receptor molecules would bind the target compound. Immunoliposomes with specific receptors for the target compound would then be introduced into the micro-chamber and allowed to bind to the immobilized target compounds. Washing buffer would be used to remove unbound immunoliposomes from the micro-chamber. Detergent would then be introduced into the micro-chamber to rupture the immunoliposomes and release the amplicons. The contents of the micro-chamber would be diverted into a reaction chamber where the amplicons would be amplified by PCR using a real-time Taqman® assay to quantitate the amount of target compound from the test sample. Fiber optic guides could be used to direct the fluorescent signal from each reaction chamber to a diode array detector for detecting the fluorescent signal generated during PCR amplification. Using this approach, a miniaturized high-throughput version of the inventive ILNAA method could be created.

A further embodiment of the invention envisions a method where antibodies or other polyvalent membrane receptors are incorporated into the outer surface of nucleic acid-containing liposomes that are unstable in the absence of these agents. An example of such liposomes would be those produced from unsaturated phosphatidylethanolamines and antibodies. Binding antigens to the membrane receptors will cause aggregation of these membrane receptors within the plane of the bilayer. This lateral phase separation will lead to the spontaneous rupture of the liposomes with the release of the entrapped nucleic acids. Isolation of the released nucleic acids from the remaining intact liposomes by centrifugation will then form the basis for the quantitation of the antigen present in the test sample by the ILNAAA method discussed above. This benefit of this modification is that no immobile phase is required for the assay.

Although several embodiments of the invention have been disclosed in the forgoing specification, it is understood by those skilled in the art that many other modifications and embodiments of the invention will come to mind to which the invention pertains, having benefit of the teaching presented in the foregoing description and associated drawings. It is therefore understood that the invention is not limited to the specific embodiments disclosed herein, and that many modifications and other embodiments of the invention are intended to be included within the scope of the invention. Moreover, although specific terms are employed herein, they are used only in generic and descriptive sense, and not for the purposes of limiting the description invention.

We claim:

1. An immunoliposome, comprising:
   a plurality of nucleic acid oligomers having identical sequences selected to correspond to a target antigen;
   an encapsulating liposome, wherein the liposome contains from 50 to 1000 copies of said nucleic acid oligomers; and
   receptors coupled to said liposome where said receptors are selected to bind with said target antigen.

2. The immunoliposome of claim 1 where the liposome is a spherical bilayer membrane defining an inner surface and an outer surface and the receptors are covalently or noncovalently bound to the outer surface of the liposomal bilayer.

3. An immunoliposome, comprising:
   a closed shell liposome;
   50 to 1,000 identical nucleic acid segments encapsulated within the liposome; and
   receptors coupled to the extravesicular surface of the liposome, wherein the receptors are selected to bind with a target analyte.

4. The immunoliposome of claim 3, wherein the receptors are selected from the group consisting of monoclonal or polyclonal antibodies, antibody Fab' fragments, glycolipids, soluble proteins, dyes, DNA probes, and RNA probes.

5. The immunoliposome of claim 3, wherein the receptors are anchored to the surface of the liposome through covalent attachment to a long-chain-length hydrocarbon having 12 to 24 carbons.

6. The immunoliposome of claim 3, wherein the long-chain-length hydrocarbon comprises carboxylic acids, amines, thiols, alcohols, aldehydes, nitrites, amides, or halides.

7. The immunoliposome of claim 3, wherein the receptors comprise electrostatically charged receptors coupled to charged lipids in the liposome.

8. The immunoliposome of claim 3, wherein protein receptors are directly incorporated into the liposome.

9. The immunoliposome of claim 3, wherein the receptors are monoclonal or polyclonal antibodies.

10. The immunolipsome of claim 3, wherein the target analyte is selected from the group consisting of proteins, nucleic acids, carbohydrates, glycolipids, gangliosides, viruses, bacteria, toxins, chemical warfare agents, explosives, poisons, hormones, cancer-specific soluble biological markers, tumor cell-surface markers, and minor cell components in larger cell populations.

11. The immunoliposome of claim 1, wherein polyethylene glycol is attached to an extravesicular surface of the encapsulating liposome.

* * * * *

SEQUENCE LISTING

```
<160> NUMBER OF SEQ ID NOS: 9

<210> SEQ ID NO 1
<211> LENGTH: 20
<212> TYPE: DNA
<213> ORGANISM: Artificial Sequence
<220> FEATURE:
<223> OTHER INFORMATION: Primer for rat beta-globin

<400> SEQUENCE: 1
ggtgcaccta actgatgttg                                              20

<210> SEQ ID NO 2
<211> LENGTH: 21
<212> TYPE: DNA
<213> ORGANISM: Artificial Sequence
<220> FEATURE:
<223> OTHER INFORMATION: Primer for rat beta-globin

<400> SEQUENCE: 2
gcttgtcaca gtggagttca c                                            21
```

<210> SEQ ID NO 3
<211> LENGTH: 23
<212> TYPE: DNA
<213> ORGANISM: Artificial Sequence
<220> FEATURE:
<223> OTHER INFORMATION: Probe for rat beta-globin

<400> SEQUENCE: 3
gataatgttg gcgctgaggg ccc                                              23

<210> SEQ ID NO 4
<211> LENGTH: 22
<212> TYPE: DNA
<213> ORGANISM: Artificial Sequence
<220> FEATURE:
<223> OTHER INFORMATION: Primer for Pneumocystis carinii

<400> SEQUENCE: 4
gatggctgtt tccaagccca tg                                               22

<210> SEQ ID NO 5
<211> LENGTH: 19
<212> TYPE: DNA
<213> ORGANISM: Artificial Sequence
<220> FEATURE:
<223> OTHER INFORMATION: Primer for Pneumocystis carinii

<400> SEQUENCE: 5
gtgacgttgc aaagtactc                                                   19

<210> SEQ ID NO 6
<211> LENGTH: 20
<212> TYPE: DNA
<213> ORGANISM: Artificial Sequence
<220> FEATURE:
<223> OTHER INFORMATION: Probe for Pneumocystis carinii

<400> SEQUENCE: 6
ataaggtaga tagtcgaaag                                                  20

<210> SEQ ID NO 7
<211> LENGTH: 23
<212> TYPE: DNA
<213> ORGANISM: Artificial Sequence
<220> FEATURE:
<223> OTHER INFORMATION: Primer for beta2-microglobin

<400> SEQUENCE: 7
tgactttgtc acagcccaag ata                                              23

<210> SEQ ID NO 8
<211> LENGTH: 20
<212> TYPE: DNA
<213> ORGANISM: Artificial Sequence
<220> FEATURE:
<223> OTHER INFORMATION: Primer for beta2-microglobin

<400> SEQUENCE: 8
aatcaaaatg cggcatcttc                                                  20

<210> SEQ ID NO 9
<211> LENGTH: 27
<212> TYPE: DNA
<213> ORGANISM: Artificial Sequence
<220> FEATURE:
<223> OTHER INFORMATION: Probe for beta2-microglobin

```
-continued

<400> SEQUENCE: 9
tgatgctgct tacatgtctc gatccca                                                            27
```